United States Patent
Murawski et al.

(10) Patent No.: US 7,862,660 B2
(45) Date of Patent: Jan. 4, 2011

(54) DEVICE AND METHOD FOR FLUID DYNAMICS CLEANING OF CONSTRAINED SPACES

(75) Inventors: Joseph J. Murawski, Plainfield, NJ (US); Yacoob Tabani, Warren, NJ (US); Mohamed Eman Labib, Princeton, NJ (US)

(73) Assignee: Princeton Trade & Technology, Inc., Princeton, NJ (US)

( * ) Notice: Subject to any disclaimer, the term of this patent is extended or adjusted under 35 U.S.C. 154(b) by 897 days.

(21) Appl. No.: 11/653,072

(22) Filed: Jan. 12, 2007

(65) Prior Publication Data
US 2008/0169005 A1 Jul. 17, 2008

(51) Int. Cl.
*B08B 9/00* (2006.01)
*B01D 61/24* (2006.01)
(52) U.S. Cl. .................. 134/8; 210/321.63; 210/321.69; 15/104.05; 15/104.096
(58) Field of Classification Search .............. 134/8, 134/42, 177, 167 R; 15/104.03, 104.05, 15/104.09, 104.095, 104.096, 246.5; 210/321.63, 210/321.69, 636
See application file for complete search history.

(56) References Cited

U.S. PATENT DOCUMENTS

| | | | |
|---|---|---|---|
| 2,222,516 A | 11/1940 | Powell et al. | |
| 3,467,314 A | 9/1969 | Grubb | |
| 3,551,331 A | 12/1970 | Cescon et al. | |
| 3,625,231 A | 12/1971 | Littrell, Jr. | |
| 3,811,408 A | 5/1974 | Thompson | |
| 3,871,913 A * | 3/1975 | Shaldon | 134/22.18 |
| 4,166,031 A | 8/1979 | Hardy | |
| 4,169,123 A | 9/1979 | Moore et al. | |
| 4,209,402 A | 6/1980 | Gentles | |
| 4,219,333 A | 8/1980 | Harris | |
| 4,311,618 A | 1/1982 | Schafer-Burkhard | |
| 4,375,413 A | 3/1983 | Geel et al. | |
| 4,380,477 A | 4/1983 | Saunders | |
| 4,400,220 A | 8/1983 | Cole, Jr. | |
| 4,444,597 A | 4/1984 | Gortz et al. | |

(Continued)

FOREIGN PATENT DOCUMENTS

DE 893595 10/1953

(Continued)

OTHER PUBLICATIONS

Azzopardi, B., "Drops in annular two-phase flow," *Int. J. Multiphase Flow*, vol. 23, Suppl., pp. 1-53 (1997).

(Continued)

*Primary Examiner*—Michael Barr
*Assistant Examiner*—Saeed T Chaudhry
(74) *Attorney, Agent, or Firm*—Merchant & Gould, P.C.

(57) ABSTRACT

A method for cleaning interior surfaces of a header region of a hemodialyzer includes steps of: introducing an insertion device having an end portion and a shaft through a hemodialyzer plug port so that the end portion of the insertion device is within the header region; rotating the shaft at a speed sufficient to generate mechanical stresses for the removal of contaminants from interior surfaces of the header region; removing the insertion device from the header region; and rinsing and flushing away the removed contaminants from the header region. An apparatus and an insertion device for cleaning a header region of a hemodialyzer are disclosed.

22 Claims, 8 Drawing Sheets

U.S. PATENT DOCUMENTS

| | | | |
|---|---|---|---|
| 4,477,438 | A | 10/1984 | Willcockson et al. |
| 4,517,081 | A | 5/1985 | Amiot et al. |
| 4,525,220 | A | 6/1985 | Sasa et al. |
| 4,622,140 | A | 11/1986 | Lee et al. |
| 4,695,385 | A | 9/1987 | Boag |
| 4,707,335 | A | 11/1987 | Fentress et al. |
| 4,710,233 | A | 12/1987 | Hohmann et al. |
| 4,744,951 | A | 5/1988 | Cummings et al. |
| 4,767,539 | A | 8/1988 | Ford |
| 4,863,688 | A | 9/1989 | Schmidt et al. |
| 4,881,563 | A | 11/1989 | Christian |
| 4,902,352 | A | 2/1990 | Christian |
| 5,007,461 | A | 4/1991 | Naf |
| 5,045,352 | A | 9/1991 | Mueller |
| 5,077,008 | A | 12/1991 | Kralovic et al. |
| 5,139,675 | A | 8/1992 | Arnold et al. |
| 5,160,548 | A | 11/1992 | Boisture |
| 5,178,830 | A | 1/1993 | Aixala |
| 5,244,468 | A | 9/1993 | Harris |
| 5,286,301 | A | 2/1994 | Albrecht |
| 5,344,652 | A | 9/1994 | Hall, II et al. |
| 5,395,456 | A | 3/1995 | Abrams et al. |
| 5,408,991 | A | 4/1995 | Iida et al. |
| 5,415,191 | A | 5/1995 | Mashimo et al. |
| 5,425,815 | A | 6/1995 | Parker et al. |
| 5,480,565 | A | 1/1996 | Levin et al. |
| 5,494,530 | A | 2/1996 | Graf |
| 5,589,507 | A | 12/1996 | Hall, II et al. |
| 5,615,695 | A | 4/1997 | Chambers |
| 5,616,616 | A | 4/1997 | Hall, II et al. |
| 5,628,959 | A | 5/1997 | Kross |
| 5,635,195 | A | 6/1997 | Hall, II et al. |
| 5,651,893 | A | 7/1997 | Kenley et al. |
| 5,656,302 | A | 8/1997 | Cosentino et al. |
| 5,658,466 | A | 8/1997 | Kawaguchi et al. |
| 5,698,100 | A | 12/1997 | Levin et al. |
| 5,714,060 | A | 2/1998 | Kenley et al. |
| 5,772,624 | A | 6/1998 | Utterberg et al. |
| 5,795,404 | A | 8/1998 | Murphy et al. |
| 5,840,343 | A | 11/1998 | Hall, II et al. |
| 5,855,216 | A | 1/1999 | Robinson |
| 5,931,845 | A | 8/1999 | Amyette |
| 5,941,257 | A | 8/1999 | Gruszczynski |
| 5,944,997 | A | 8/1999 | Pedersen et al. |
| 5,961,937 | A | 10/1999 | Gobbato |
| 6,027,572 | A | 2/2000 | Labib et al. |
| 6,050,278 | A | 4/2000 | Arnal et al. |
| 6,179,954 | B1 | 1/2001 | Kawana et al. |
| 6,192,900 | B1 | 2/2001 | Arnal et al. |
| 6,193,890 | B1 | 2/2001 | Pedersen et al. |
| 6,207,201 | B1 | 3/2001 | Piacenza |
| 6,261,457 | B1 | 7/2001 | Wenthold et al. |
| 6,326,340 | B1 | 12/2001 | Labib et al. |
| 6,423,152 | B1 | 7/2002 | Landaas |
| 6,454,871 | B1 | 9/2002 | Labib et al. |
| 6,619,302 | B2 | 9/2003 | Labib et al. |
| 6,823,881 | B1 | 11/2004 | Mishkin et al. |
| 6,857,436 | B2 | 2/2005 | Labib et al. |
| 6,945,257 | B2 | 9/2005 | Tabani et al. |
| 2004/0007255 | A1 | 1/2004 | Labib et al. |
| 2006/0144776 | A1* | 7/2006 | Mishkin et al. ........ 210/321.69 |

FOREIGN PATENT DOCUMENTS

| | | | |
|---|---|---|---|
| EP | 490117 | A1 | 6/1992 |
| EP | 213157 | B1 | 10/1992 |
| EP | 160014 | B1 | 1/1993 |
| EP | 289523 | B1 | 1/1995 |
| EP | 634229 | B1 | 1/1995 |
| JP | 11-104636 | | 4/1999 |
| SU | 1042826 | A | 9/1983 |
| WO | WO 85/01449 | | 4/1985 |
| WO | WO 86/05116 | | 9/1986 |
| WO | WO 88/00494 | | 1/1988 |
| WO | WO 95/10349 | | 4/1995 |
| WO | WO 98/58632 | | 12/1998 |
| WO | WO 99/29401 | | 6/1999 |

OTHER PUBLICATIONS

Barajas, A. et al., "The effects of contact angle on two-phase flow in capillary tubes," *Int. J. Multiphase Flow*, vol. 19, No. 2, pp. 337-346 (1993).

Cameron, A., Basic Lubrication Theory, 3rd Edition, pp. 37-51, 93-125, John Wiley & Sons, New York, NY, (1981).

Fuller, D.D., Theory and Practice of Lubrication for Engineers, 2nd Edition, pp. 198-296, John Wiley & Sons, New York, NY, (1984).

Hays, "A Variational Approach to Lubrication Problems and the Solution of the Finite Journal Bearing," J. Basic Eng., 81:13-23 (1959.

Henstock, W. et al., "The Interfactial Drag and the Height of the Wall Layer in Annular Flows," *AIChE Journal*, vol. 22, No. 6, pp. 990-999 (Nov. 1976).

Hewitt, G. et al., "Annular Two-Phase Flow," *Pergamon Press*, pp. v-vii, 1-20, chapters 1-2 (Date Unknown).

Hobbe et al. "Use of Nuclepore Filters for Counting Bacteria by Fluorescence Microscopy," *Appl. and Environ. Microbiol.*, vol. 33, No. 5, pp. 1226-1228 (May 1977).

Hubbe, "Detachment of Colloidal Hydrous Oxide Spheres From Flat Solids Exposed to Flow 1. " Experimental System, Colloids and Surfaces, 16:227-248 (1985).

Hubbe, "Detachment of Colloidal Hydrous Oxide Spheres From Flat Solids Exposed to Flow 2." Mechanism of release, Colloids and Surfaces, 16:249-270 (1985).

Hubbe, "Detachment of Colloidal Hydrous Oxide Spheres From Flat Solids Exposed to Flow 3." Forces of adhesion, Colloids and Surfaces, 25:311-324 (1987).

Hubbe, "Theory of Detachment of Colloidal Particles From Flat Surfaces Exposed to Flow," Colloids and Surfaces, 12:151-178 (1984).

Kabin, et al., "Removal of Solid Organic Films From Rotating Disks Using Emulsion Cleaners," J. of Colloid and Interface Sci., 228:344-358 (2000).

Klauer, J., "Piping: An examination of pipe self cleaning in high-purity water systems," *Ultrapure Water*, pp. 56-60 (Mar. 2001).

Kogure et al., "A tentative direct microscopic method for counting living marine bacteria," *Can. J. Microbiol.*, vol. 25, pp. 415-420 (1997).

Leal, L.G., Laminar Flow and Convective Transport Processes: Scaling Principles and Asymptotic Analysis, pp. 396-406, Butterworth-Heinemann, Newton, MA, (1992).

Lee, et al., "Motion of a Sphere in the Presence of a Plane Interface. Part 1. An Approximate Solution by Generalization of the Method of Lorentz," J. Fluid Mech., 93:705-726 (1979).

Lee, et al., "Motion of a Sphere in the Presence of a Plane Interface. Part 2. An Exact Solution in Bipolar Co-Ordinates," J. Fluid Mech., 98:193-224 (1980).

Leypoldt, John K. & Cheung, Alfred K., "Characterization of Molecular Transport in Artificial Kidneys," Artifical Organs, International Socity for Artificial Organs, vol. 20, No. 5, pp. 381-389, Jan. 1996.

Reinemann, D., "Dairy operators guide to milking machine cleaning and sanitation," *Paper written for presnetation at the NRAES the Milking Systems and Parlors Conference*, 8 pages (Jan. 30, 2001).

Reynolds, "On the Theory of Lubrication and Its Application to Mr. Beauchamp Tower's Experiments, Including Experimental Determination of the Viscosity of Olive Oil," Philosophical Transactions of the Royal Society of London, England, 177:157-234 (1887).

Riedewald, F., "Biofilms in Pharmaceutical Waters," *Pharmaceutical Engineering*, 8 pages (Nov./Dec. 1997).

Ryan, et al., "Colloid Mobilization and Transporting Ground Water," Colloids and Surfaces, 107:1-56 (1996).

Tragardh, C., "Cleaning in air-water-flow," *Division of Food Engineering, Lund Engineering, Alnarp* (Sweden), pp. 424-429 (Date Unknown).

Triplett, K. et al., "Gas liquid two-phase flow in microchannels. Part 1: two-phase flow patterns," *International Journal of Multiphase Flow*, vol. 25, pp. 377-380, 387-393 (1999).

Truskey, et al., "Relationship Between 3T3 Cell Spreading and the Strength of Adhesion on Glass and Silane Surfaces," Biomater, 14(4):243-254 (1993).

Truskey, et al., "The Effect of Fluid Shear Stress Upon Cell Adhesion to Fibronectin-Treated Surfaces," J. Biomed. Mater. Res., 24:1333-1353 (1990).

Web page print-out "510(k) Premarket Notification Database", 8 pages (Jan. 5, 2006).

Woodmansee, D. et al., "Mechanism for the removal of droplets from a liquid surface by a parallel air flow," *Chemical Engineering Science*, vol. 24, pp. 299-307 (1969).

Yiantsios, et al., "Detachment of Spherical Microparticles Adhering on Flat Surfaces by Hydrodynamic Forces," J. of Colloid and Interface Sci., 176:74-85 (1995).

* cited by examiner

Fig. 5
TYPE A
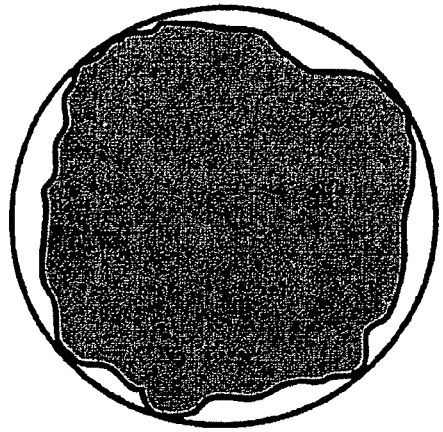
TYPE B
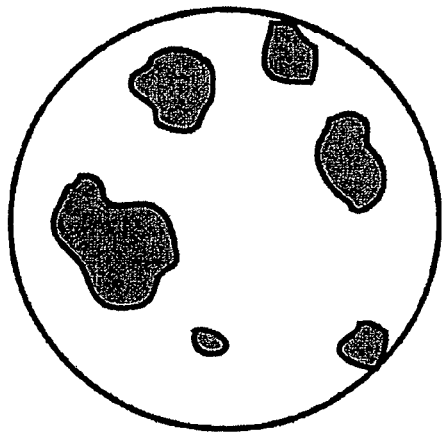
TYPE C
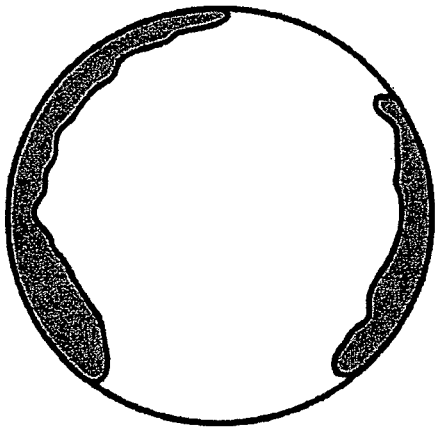
TYPE D
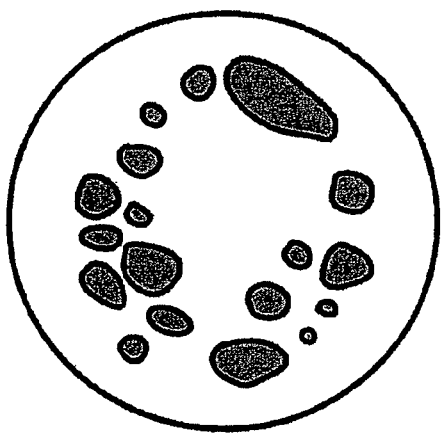
TYPE E
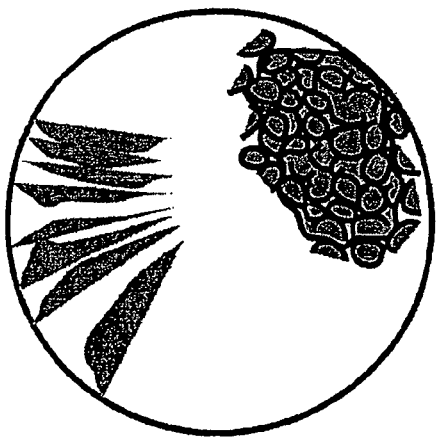

DEVICE AND METHOD FOR FLUID DYNAMICS CLEANING OF CONSTRAINED SPACES

FIELD OF THE INVENTION

This invention relates to cleaning of constrained spaces, cavities and surfaces by creating fluid dynamics flow fields and generating mechanical stresses sufficient to achieve cleaning or surface modifications.

BACKGROUND OF THE INVENTION

Cleaning internal cavities is a difficult process. Large pipes, tanks, and other symmetrical cavities are mechanically cleaned by brushes, flails, and high pressure jets (e.g., liquid, gas, or steam). There is much poorer access to applying necessary mechanical action to smaller or complex-shaped internal cavities especially where materials transport becomes increasingly difficult. Brushes such as described by U.S. Pat. No. 5,931,845 to Amyette and dental flossers such as described by U.S. Pat. No. 5,855,216 to Robinson are designed to primarily remove material by direct mechanical contact where the contaminants are mostly removed by direct materials transfer, including scraping, displacement and the like. These methods require physical contact between a solid flexible member or element and the surface to be modified or cleaned, and are therefore limited to cleaning approximately cylindrical or accessible internal cavities.

Liquid/air jets as described by U.S. Pat. No. 6,192,900 to Arnal, et al. increase the cleanable areas of an internal cavity, but still require line of site accessibility from the jet orifice and a source of high pressure; therefore, the cleaning is always incomplete and in most cases requires complex alignment systems. Further, without the added presence of a moving solid member or element that could access the entire area to be cleaned, these liquid/jet cleaning methods have difficulty removing and homogenizing large debris such as blood clots, particulate materials, organic contaminants and the like. See U.S. Pat. No. 4,375,413 to Geel, et al. and U.S. Pat. No. 6,823,881 to Mishkin et al.

Multiple flow cleaning methods are described. For example, see U.S. Pat. No. 6,027,572 to Labib, et al., U.S. Pat. No. 6,326,340 to Labib, et al., U.S. Pat. No. 6,454,871 to Labib, et al., U.S. Pat. No. 6,619,302 to Labib, et al., U.S. Pat. No. 6,857,436 to Labib et al., U.S. Publication No. 2004/7255 to Labib, et al., and U.S. Pat. No. 6,945,257 to Tabani, et al. which are incorporated by reference herein. Multiple phase flow improves the cleanable areas of high-aspect ratio internal cavities, especially those with a high length/diameter (L/D) ratio, i.e., long and narrow spaces. Multiple phase flow can be complemented in large low-aspect ratio internal cavities with massive deposits, and wide and shallow spaces. Large low-aspect ratio designated cavities where L/D is small include hemodialyzer header space, hollow fiber modules headers, flat or curved surfaces where a cavity may be created to effect the cleaning of such surfaces, and the like.

Even though liquid/gas techniques can often access more of the internal surfaces better than moving solid devices alone, such as those described above, it would be beneficial if these methods could be combined. Liquid/gas flow inside cavities and spaces is insufficient to clean the same since such flow cannot generate sufficient shear stress to remove all the contaminants from all locations. It would be even more effective if this combination could be further improved to create optimal hydrodynamic flow fields within the cavity such that the generated mechanical stresses would be capable of completely cleaning the entire surfaces of internal cavities.

The theory of hydrodynamic flow and its effect on surface interactions has been elaborated for the case of a rotating disk. For example, see Cabin, et al., "Removal of Solid Organic Films From Rotating Disks Using Emulsion Cleaners," J. of Colloid and Interface Sci., 228:344-358 (2000) and Yiantsios, et al., "Detachment of Spherical Microparticles Adhering on Flat Surfaces by Hydrodynamic Forces," J. of Colloid and Interface Sci., 176:74-85 (1995). The theory of colloid mobilization was studied by Ryan, et al., "Colloid Mobilization and Transporting Ground Water," Colloids and Surfaces, 107:1-56 (1996), using glass spheres or latex particles. There are few papers devoted to the removal of biocontamination. See Truskey, et al., "Relationship Between 3T3 Cell Spreading and the Strength of Adhesion on Glass and Silane Surfaces," Biomater, 14(4):243-254 (1993), and Truskey, et al., "The Effect of Fluid Shear Stress Upon Cell Adhesion to Fibronectin-Treated Surfaces," J. Biomed. Mater. Res. 24:1333-1353 (1990). However, these studies of basic theory have not been adapted or modified for cleaning the surfaces of internal cavities. In addition, such theories do not address the different flow patterns or modes of creating shear or other mechanical stresses in small cavities. It would be beneficial to extend hydrodynamic theory to the cleaning of poorly accessible internal surfaces such as in the case of hemodialyzer headers and the like.

Cleaning reusable dialyzer membranes is one application that needs improvement. Patients with End-Stage Renal Disease (ESRD) or who have acute or chronic renal failure, have kidneys that are incapable of removing waste products of metabolism and other substances from the blood and of excreting such undesirable substances in the urine. Patients with ESRD or persons who suffer from other forms of acute or chronic renal failure require dialysis treatments or kidney transplants. Only a small percentage of patients with renal failure are fortunate to receive kidney transplants, while the rest and the majority must undergo a form of dialysis treatment to purify their blood on a periodic basis.

Dialysis is defined as the process of cleaning wastes from the blood artificially. The two major forms of dialysis are hemodialysis and peritoneal dialysis. In hemodialysis, the blood travels through tubes to a dialyzer (also called hemodialyzer), which removes wastes and extra fluid from a patient's blood. The cleaned blood then flows through another set of tubes back to the body. This treatment can be performed three times per week, or even more times depending on the country and the healthcare system. In the year 2000, there were about 375,000 patients undergoing hemodialysis treatment and only about 40,000 receiving peritoneal treatment in the U.S. The number of patients requiring hemodialysis treatment is on the rise mostly because of the prevalence of Type II diabetes. The number of patients is increasing at a rate of about 8-10% per year. The number of patients requiring hemodialysis in the United States is expected to reach 600,000 by 2010. Hemodialysis treatment is the largest program funded by Medicare in the U.S. The majority of funding for dialysis treatment in the U.S. is in the form of reimbursement (e.g., $130/dialysis treatment/patient). Decreasing the cost of hemodialysis treatment is of paramount importance. It is also desirable to provide better overall treatment to dialysis patients while simultaneously improving the profitability of dialysis centers. A significant cost of hemodialysis treatment is the dialyzer which needs to be reprocessed to allow for multiple uses by the same patient. The number of treatments or uses of the same dialyzer is referred to as the "reuse number." The practice of reusing dialyzers is permitted in the United States and many other countries. Dialyzer reuse is practiced in more than 70% of dialysis centers in the United States. Reuse is also beneficial because it cuts the amount of waste produced, which is both an economic (saves on the cost of disposal) and environmental (less waste) benefit. Since the dialyzer is not degradable and requires special biodisposal methods such as incineration, other environmental issues plus disposal costs are anticipated. It is therefore desirable to develop new methods and devices to achieve more efficient dialyzer reprocessing to reduce the cost and environmental impact, and at the same time to provide better-dialysis treatment for ESRD patients The dialyzer is the device that effects the removal of fluids and wastes from a patient's blood. The dialyzer has two sections or compartments separated by a semi-permeable membrane. One section holds the dialysis solution (sometimes referred to as the dialysate) and the other holds the patient's blood. The dialyzer section that holds the dialysate is called the dialysate compartment and the section that holds the patient's blood is termed the blood compartment. The two compartments are in communication with each other through a semi-permeable membrane where waste substances such as urea and creatinine diffuse out from the blood side to the dialysate side of the dialyzer. Such diffusion and transport processes are the basis of dialysis treatment for patients that lack kidney function. The semi-permeable membranes of some types of dialyzers (termed high-flux dialyzers) are also capable of performing ultrafiltration, and this function is used to remove excess water from the patient's body during dialysis. By adjusting the pressure difference between the blood and dialyzer compartments with the aid of the dialysis machine, excess body water is removed during dialysis treatment.

In order to achieve dialysis treatment in a reasonable period of time, the membrane surface area of the dialyzer must be large enough to accomplish its task in the targeted time frame. A membrane surface area of approximately 1.5 to 2.5 square meters was found to be reasonable to achieve full dialysis treatment in about 3.5 to 4.4 hours. In order to package such a large membrane surface area in a dialyzer of a practical size, the hollow fiber membrane module configuration offers the optimal geometry. In this configuration, the membrane surface area needed is obtained by using a large number of small-diameter hollow fibers that are constructed from semi-permeable membranes.

A typical dialyzer has in excess of 12,000 of these hollow fibers, which are usually present in the form of a bundle of fibers (bundle diameter is about 3-5 cm) encased in a cylindrical rigid plastic shell, called a housing. During manufacturing, the extruded hollow fiber bundle is introduced into the rigid plastic shell housing and both ends of the fiber bundle are then embedded in a special polyurethane resin to completely fill the spaces between the fibers in the bundle and to seal the entire space with the plastic shell. After the resin is cured, the fiber bundle is cut on both ends of the plastic shell housing. Current manufacturing steps are designed to ensure that all fibers are open from both sides and that complete separation between the inside of fibers and the plastic shell housing is accomplished. The dialyzer is then outfitted with two headers or caps, one on each end, to provide access for the blood to flow into and out of the dialyzer during the dialysis treatment. These headers may be removable or made as a permanent part of the body of the dialyzer, depending on the manufacturer.

Each dialyzer is tested to satisfy the absolute condition of separation between the blood and dialysate compartments and other attributes; all testing is a part of the elaborate quality control process. Dialyzers cost between $12-30, depending on the type. Dialyzers are labeled either as "single use" or "for reuse (multiple uses)." Single-use dialyzers are discarded after each dialysis treatment, while reuse dialyzers are reprocessed after each dialysis session and reused by the same patient until they fail a critical criterion set by the FDA. On the average, a single-use high-flux dialyzer costs about $10-15 and a reuse high-flux dialyzer costs $25-30.

In reuse hemodialysis, a dialyzer is issued to the patient and reprocessed (cleaned and sterilized) after each dialysis treatment and then reused by the same patient until the dialyzer fails certain criteria set-forth by the FDA or additional criteria set by the dialysis center performing the treatment. Reuse dialyzers fail, or become unusable, for four basic reasons: (1) when the blood volume compartment of the dialyzer decreases to less than 80% of its new value, (2) if the dialyzer develops fiber leaks, (3) when the dialyzer's appearance becomes objectionable due to accumulated blood clots inside the fiber bundle or in the header region, or (4) when the number of reuses exceeds an arbitrary maximum reuse number set by the dialysis center. The FDA requires that reused dialyzers must have total cell volume or TCV (or blood volume inside the fiber bundle) above 80% that of a new dialyzer to ensure that 90% of urea is cleared during the treatment, that no fiber leaks occur during dialysis, and that the dialyzer be preserved in an approved liquid sterilant for more than 13 hours prior to the dialysis session to avoid subjecting the patient to microbial contamination. The dialyzer reuse number varies based on patient condition, reprocessing method, reagents used in reprocessing, protocol used to clean the header region (the pre-cleaning steps), and other factors, including the use of heparin during dialysis and handling the dialyzer after dialysis treatment. Dialyzer reuse practice is approved in the United States and Canada and in many countries in Asia and Latin America, but is not allowed in Japan and many European Union Countries, which adopt single-use dialysis where the dialyzer is disposed of after each treatment. Due to cost pressures, many countries are now practicing or considering adopting dialyzer reuse (reprocessing) to cut the cost of dialysis treatment.

Historically, the average dialyzer reuse number was about 3-5 when the reuse practice first started in the middle of the 1980s. This reuse number has increased in recent years by improving the dialyzer, preventing clotting during dialysis by heparinization and by adopting strict protocols to manually pre-clean the dialyzers prior to reprocessing them with automated devices. Many dialysis centers have instituted protocols to use heparin during dialysis to prevent the formation of blood clots inside the dialyzer (inside the fibers and header regions) during the dialysis session. Other dialysis centers require infusing a certain volume of heparin solution into the dialyzer immediately after the conclusion of treatment to minimize the formation of blood clots in the dialyzer until it is reprocessed. In addition, protocols now call for reprocessing the dialyzer within a short period of time after the treatment, usually two hours. All these attempts are made to increase the average reuse number of hemodialyzers.

Manual pre-cleaning of the dialyzer before reprocessing it with an automated device has been a very significant parameter responsible for improving the number of reuses, currently in the range of 8-15. This manual pre-cleaning of the dialyzer is an essential step that is needed prior to reprocessing with a peracetic acid liquid sterilant such as Renalin®, or other types of reprocessing, including the bleach formaldehyde process. Peracetic acid is known to denature blood proteins and increase the adhesion of blood components to the internal surfaces of the dialyzers, including the surfaces of hollow fibers, the header region cavity, as well as the O-ring that is present in dialyzers that have removable end caps. Current industry standard reprocessing devices, such as the Renatron® made by Minntech Corporation, do not have the capability to effectively clean the header region of a dialyzer. Due to these limitations, manual header cleaning is practiced to remove residual blood from the dialyzer by introducing reverse osmosis water into the fiber bundle and by using backflushing where water enters the blood compartment by pressurization of the dialysate compartment. Usually such cleaning does not follow a specific protocol and is left to the discretion of the technician.

An important step in reprocessing the dialyzer is manual pre-cleaning, which involves removing a range of blood clots from the header region of the dialyzer. Without removing such clots, the dialyzer cannot be successfully reprocessed, and will have a greater chance of failing prematurely for one of the 4 reasons stated above, specifically appearance and TCV. Header cleaning is possibly the most demanding step in pre-cleaning the dialyzer before using automated reprocessing machines. It requires, in many instances, hitting or impacting the external sides of the dialyzer end cap with a hard blunt object in order to dislodge blood clots present inside the header region of the dialyzer. A rawhide mallet tends to be the tool of choice. In some cases, reprocessing technicians often introduce "unsterile or contaminated" foreign objects inside the header to remove stubborn blood clots, and in most cases the same object is used to handle the dialyzers of multiple patients. A paperclip is a known object that is used to carry out this job. This kind of intervention has the potential of compromising the integrity of the dialyzer and increases the risk of cross infection between hemodialysis patients. Furthermore, in many cases the header is removed and the dialyzer and its cap are cleaned separately to remove blood clots. This practice is now discouraged due to the occurrence of an incident where 18 patients fell very ill, and where the CDC determined that this episode was due, to microbial contamination due to removing the header of the dialyzer during reprocessing. This incident and the associated practice are now known as "Header Syndrome." Inability to remove blood from the dialyzer headers prior to reprocessing results in low reuse numbers. Blood clots in dialyzer headers are formed during dialysis treatment due to accumulation and stagnation of a volume of blood over an extended period of time, about three to four hours.

The presence of O-rings in some dialyzer models, such as Fresenius® F80A and F80B, and Optiflux® 180A, 180B, 200A and 200B introduces additional difficulties during reprocessing since blood clots could be entrapped behind or underneath the O-ring. Additionally, such O-rings create areas of dead flow that hamper effective cleaning of the header. To overcome this problem, the technician often removes the end cap and O-ring and cleans the end cap, O-rings, and puttied dialyzer surface manually. Due to the complex nature of blood clotting inside dialyzer headers, both manual and automated pre-cleaning devices, such as the RenaClear® made by Minntech Corporation, have many limitations, and this problem has been rendered even more complicated due to the fact that different dialyzer models have different header geometry. To complicate the issue, recent dialyzer designs have moved away from removable end caps, and dialyzers with O-ring-free headers are molded with the outer shell and thus cannot be removed during manual cleaning.

Blood clots inside the dialyzer header have many adverse consequences that influence the probability of successfully reprocessing the dialyzer and making it reusable. If the header contains large clots that cannot be removed or cleaned during the pre-cleaning step, subsequent reprocessing with one of the current devices, such as the Renatron® (made by Minntech Corporation, Minneapolis, Minn.) or the Seratronics® (made by Fresenius Medical Care, Lexington, Mass.) will not be successful. Often, the total cell volume of such dialyzers cannot be recovered to the FDA-required 80% level. When significant header clots are present during automated reprocessing, it is impossible to pass liquids through the hollow fibers because the openings of such fibers are blocked by blood clots in the header regions. This obstruction may be present on the inlet, the outlet, or both sides of the hollow fiber bundle, i.e., the venous side, arterial side, or both.

Dialyzers with highly clotted headers are so difficult to reprocess that in many cases they are discarded even without attempting to pre-clean them, let alone reprocess them. According to protocols adopted by many dialysis centers, the unacceptable appearance of a dialyzer due to the presence of large blood clots in the headers is sufficient to fail the dialyzer. Therefore, the presence of blood clots in the header region of the dialyzer constitutes a major problem that demands innovative methods and devices to overcome. The labor cost expended in pre-cleaning dialyzer headers is considerable and the risk of exposing reprocessing technicians to patient materials and infection needs to be eliminated, or greatly minimized.

Attempts to find a satisfactory means of cleaning the dialyzer header region can be complex, costly and time consuming. The RenaClear® device, manufactured by Minntech Corporation, is an example of such a device. This complicated and expensive device performs the header pre-cleaning steps as described by U.S. Pat. No. 6,192,900 to Arnal, et al. Using the RenaClear® device involves attaching the dialyzer to a device that introduces a jet of liquid from a needle where the jet is propelled with a stream of air. The jet is applied intermittently with the position of the jet direction changing with the aid of a motor. The jet action effects dislodging of blood clots due to the mechanical impact forces of the liquid, and the dislodged clots inside the header are then removed through a fluid path around the needle, again with the action of air/suction.

The RenaClear® device uses a peracetic acid solution to clean the header; such a process may require several minutes to perform, including attaching and detaching the dialyzer. The action of the jet is not very precise due to the geometrical complexity of the header and the possibility of bending the needle during handling. If the needle is bent, the direction/trajectory of the jet becomes less precise and the cleaning achieved becomes sub-optimal. In addition, cleaning of the entire internal surface of the header is impossible due to shadowing effects of obstructions inside the header, such as the O-ring, and to directional distortion due to the bending of the needle. An example of shadowing effects is exemplified by lack of cleaning in the regions that are shadowed by the O-ring, including the O-ring itself. Moreover, the RenaClear® device may be a source of contamination where blood clots can be forced to enter underneath and become lodged behind the O-ring due to the action of the jet, or in some cases even moved to other locations of the header and re-deposited. A major problem with the RenaClear® device is often associated with "bending the needle" during use, and this is due to the difference in header dimensions (tolerance) and frequent manipulation of the device, which involves attaching and detaching the dialyzer before actual reprocessing. In addition to the time consumed during header cleaning, the Rena- Clear® device requires the use of additional peracetic acid reagent during this pre-cleaning step, further adding to the cost of dialyzer reprocessing.

After subjecting the dialyzer to pre-cleaning using manual cleaning or the RenaClear® device, the dialyzer is removed and then installed for reprocessing with the Renatron® device, which performs the remaining tasks of reprocessing the dialyzer, including measuring TCV, testing for fiber leaks and filling the dialyzer with the peracetic acid liquid sterilant. The practice of installing and removing the dialyzer from two devices requires additional labor and time. This adds to reprocessing time, labor cost, and additional costs due to the use of reprocessing liquids and RO water. This is in addition to the high capital and maintenance costs of two separate devices for reprocessing the dialyzer.

It would be beneficial to find a better way to properly, repeatedly and consistently clean the headers of dialyzers and other difficult-to-access internal cavities found in applications such as water treatment, industrial processing, filtration, housings, in-line processing, bioprocessing, medical and dental devices, sensors, food processing, manufacturing and the like.

SUMMARY OF THE INVENTION

A device and method for cleaning hard to access cavities, spaces and surfaces are provided. A special moving member or element can induce a fluid dynamics flow field and generate sufficient shear and other mechanical stresses as it moves within the internal spaces of cavities of different shapes. The flow field is capable of creating a turbulent flow of gases and liquids sufficient to generate shear and other mechanical stresses to remove surface contaminants from the internal cavity. One embodiment of the method includes reprocessing medical devices, including membrane modules and other articles that contain at least one difficult to clean cavity or space where, during normal operation, blood, biological or organic matter, patient residues, food substances, debris and other contaminants may accumulate, and where such materials need to be removed and cleaned to allow successful reuse of such devices. In another embodiment, the invention relates to a device and method for pre-cleaning and cleaning the headers of hemodialyzers and hemofilters, and specifically the internal surfaces of such headers. This embodiment also includes cleaning the header regions of membrane modules such as those used in other applications, including water treatment, food and fluid processing, biopharmaceuticals, and similar industrial processing. The invention further addresses the cleaning of cavities and spaces that may not include a membrane as part of the device or equipment where the fluid dynamics of the cleaning disclosed here are deemed applicable. Further, the invention provides means for cleaning and sampling surfaces, such as those of pharmaceutical equipment, by applying fluid flow fields to produce efficient shear stresses and materials transfer from such surfaces for the purpose of cleaning, analysis and quality control.

A method for cleaning interior surfaces of a header region of a hemodialyzer is provided according to the invention. The method includes steps of: introducing an insertion device having an end portion and a shaft through a hemodialyzer blood port so that the end portion of the insertion device is within the header region; rotating the shaft at a speed sufficient to generate mechanical stresses for the removal of contaminants from interior surfaces of the header region; removing the insertion device from the header region; and rinsing and flushing away the removed contaminants from the header region.

A method for cleaning interior surfaces of an enclosed cavity having a neck is provided according to the invention. The method includes steps of: introducing an insertion device having an end portion and a shaft through the neck so that the end portion of the insertion device is within the enclosed cavity; rotating the shaft at a speed sufficient to generate mechanical stresses sufficient to remove contaminants from the interior surfaces of the cavity; removing the insertion device from the cavity; and rinsing and flushing away the removed contaminants from the cavity.

An apparatus for cleaning a header region of a hemodialyzer is provided according to the invention. The apparatus includes an insertion device having an end portion and a shaft and constructed for insertion through a hemodialyzer blood port so that the end portion can be provided within the header region of the hemodialyzer; a rotating motor constructed to rotate the shaft of the insertion device; and a hemodialyzer blood port connection constructed for stabilizing the insertion device when the end portion is within the header region of the hemodialyzer.

An insertion device for use in cleaning a header region of a hemodialyzer is provided according to the invention. The insertion device includes an end portion, a shaft, and a bend in the shaft, wherein the end portion and the shaft are constructed for insertion through a hemodialyzer blood port so that the end portion can be provided within the header region of the hemodialyzer and, when the shaft is rotated, the end portion can generate mechanical stresses for the removal of contaminants from interior surfaces of the header region.

BRIEF DESCRIPTION OF THE DRAWINGS

FIG. 5 shows different types of clots;

DETAILED DESCRIPTION OF THE INVENTION

Figure 1A:
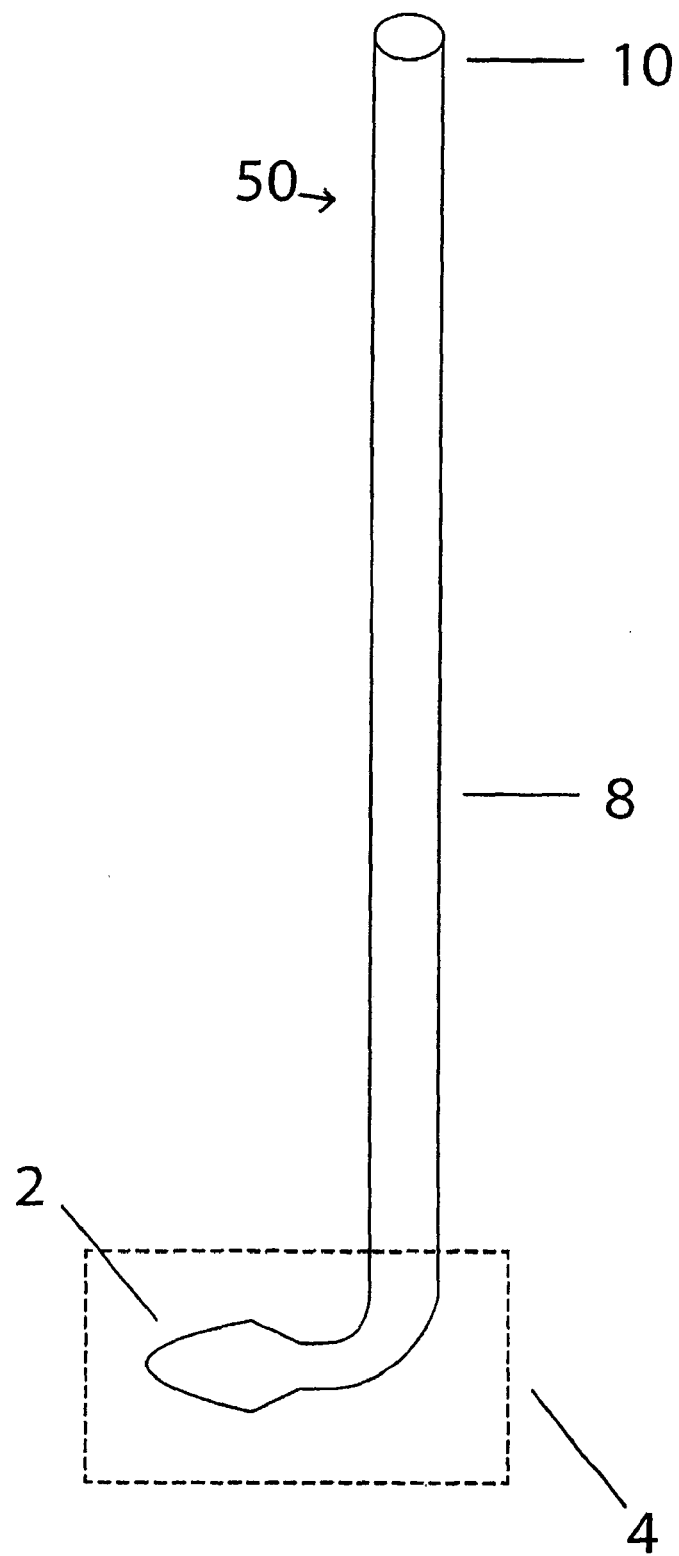
FIG. 1*a* is a schematic of an insertion device (ID)

The present invention describes novel devices and methods based on harnessing certain types of fluid dynamics to clean or otherwise modify surfaces. The devices and methods of the present invention are effective, less costly, less time consuming, and potentially provide better cleaning than the art. The ability to clean poorly accessible surfaces (e.g., internal cavities) demonstrates one of the improvements of this invention over the art. This invention also improves over the art through a different approach and additional steps of indirectly overcoming forces of surface adhesion by using fluid dynamics criteria to design and employ a flexible member compatible with the shape of an interior cavity, and a design to impart controlled turbulent flow and flow fields, and to create sufficient mechanical stresses within a gas, liquid or their mixtures in the interior cavity.

The use of the terms interior cavity, cleaning, rotation, and surface cleaning or modification describe particular embodiments and are not meant to limit the overall invention. Some non-limiting examples can include surface modification other than cleaning, modification of exterior surface, linear sweeping instead of rotation, axial rotation combined with angular rotation, superimposed induced vibrations, etc.

Alphabetic List of Symbols a shorter side of a rectangular insertion device (ID) or radius of a cylindrical ID (cm)
B housing radius (cm)
b longer side of a rectangular ID (cm)
$b_{cr}$ critical cross-section of a rectangular ID with longer side b (cm)
$D_o$ diameter of the access port (cm)
d diameter of cylindrical model of ID (cm)
E modulus of elasticity or Young's modulus
f rotational frequency (Hz)
f(u) frequency of liquid rotation (Hz)
H linear dimension, characterizing the width of the liquid stream. H=l within the gap and H=$h_c$ for the liquid stream flow outside the gap. For water, $h_c$ is typically ~3 mm
$h_c$ height of the internal cavity or the height of the liquid (cm)
h cavity (e.g., dialyzer header) height
$h_o$ the minimum value of h
h(z) height in the z direction
I moment of inertia
K a constant used in Equations 10 and 12
L ID length
l gap distance between the ID and the main surface to be cleaned (cm)
l(r) length along the radial direction
l(z) gap in the z-direction; $l_o$<l(z)<d/2
$l_s$(r) theoretical gap distance between a straight rigid ID and the main surface to be cleaned, at a particular radius r (cm)
$l_s(R_1)$ theoretical gap at r=$R_1$
$l_o$ minimum gap (cm)
P pressure
R radius of the main circular surface to be cleaned (cm)
$R_1$ radius corresponding to the boundary layer between zone r<$R_1$ where ID bending is strong and zone r>$R_1$ where ID is almost straight
Re Reynolds number
$Re_{cr}$ Critical Reynolds number
r radial distance to the axis of rotation, between 0 and R (cm)
T couple, moment
$T_g$ Glass transition temperature
$U_\phi$ azimuthal velocity of liquid in cavity
u azimuthal velocity of rotating liquid
u(r) radial dependence of u
V simplified nomination for v(r)
$V_\phi(z)$ local ID velocity with respect to the immobile surface for a symmetrical cylindrical ID surface
V(x,z) velocity distribution in the gap in lubrication approximation
$V_r$ radial velocity in cavity
$V_f$ velocity inside the hollow fibers
$V_z$ z component of velocity distribution, V(x,z)
$V_x$ x component of velocity distribution, V(x,z)
v azimuthal velocity of the ID
v(r) radial dependence of azimuthal velocity of ID
W uniform distributed load
x coordinate perpendicular to main cleaning surface inside gap between it and ID
X X=1−r/B
$y_{max}$ maximum ID deflection
z R−r
Z coordinate perpendicular to mobile and immobile disk in the model of rotating disk
α angle ID is bent from rotor axis (degrees)
$α_o$ angle (degrees)
δ boundary layer thickness for a rotating ID
$δ_o$ boundary layer thickness for a housing
δ(u) average hydrodynamic boundary layer thickness on the surface to be cleaned
δ(v) average hydrodynamic boundary layer thickness on the ID surface
η dynamic viscosity
θ angle with the axial direction of the ID
τ shear stress on the immobile surface
$τ_u$ viscous stress on the surface to be cleaned
$τ_v$ viscous stress on the ID surface
$τ_w$ shear stress at the wall
$τ(R_1)$ shear stress at $R_1$
$τ(R_2)$ shear stress at $R_2$
τ(z) shear stress in the z direction
ν kinematic viscosity
ω angular frequency 2πf
ω* angular frequency 2πf=0.54ω
φ azimuthal angle Abbreviations Dialyzer Hemodialysis filter cartridge
ESRD End-Stage Renal Disease
FDA U.S. Food and Drug Administration
Gap Distance between the ID and a defined surface
ID Insertion Device
MCS Main Cleaning Surface
PAA Peracetic Acid
RO Reverse Osmosis
SAA Surface Active Agent
TCV Total Cell Volume
TPA Tissue Plasminogen Activator—a medication used to dissolve blood clots Surfaces, Cavities, Spaces and their Modification The present invention excels at modifying certain types of surfaces. While planar circular surfaces are preferred, other surfaces (e.g., cylinder interiors, planar surfaces, rectangular channels, cup interiors and others), where a fluid flow field can be created with the aid of a movable member, are envisioned. The root mean square (RMS) average surface roughness is preferably less than the thickness of the liquid boundary layer present at the surface under the flow conditions prevailing during the application of flow fields of this invention. This condition ensures that any surface protrusions will not cause impinging action with this invention's movable member or insertion device (ID).

Figure 2:
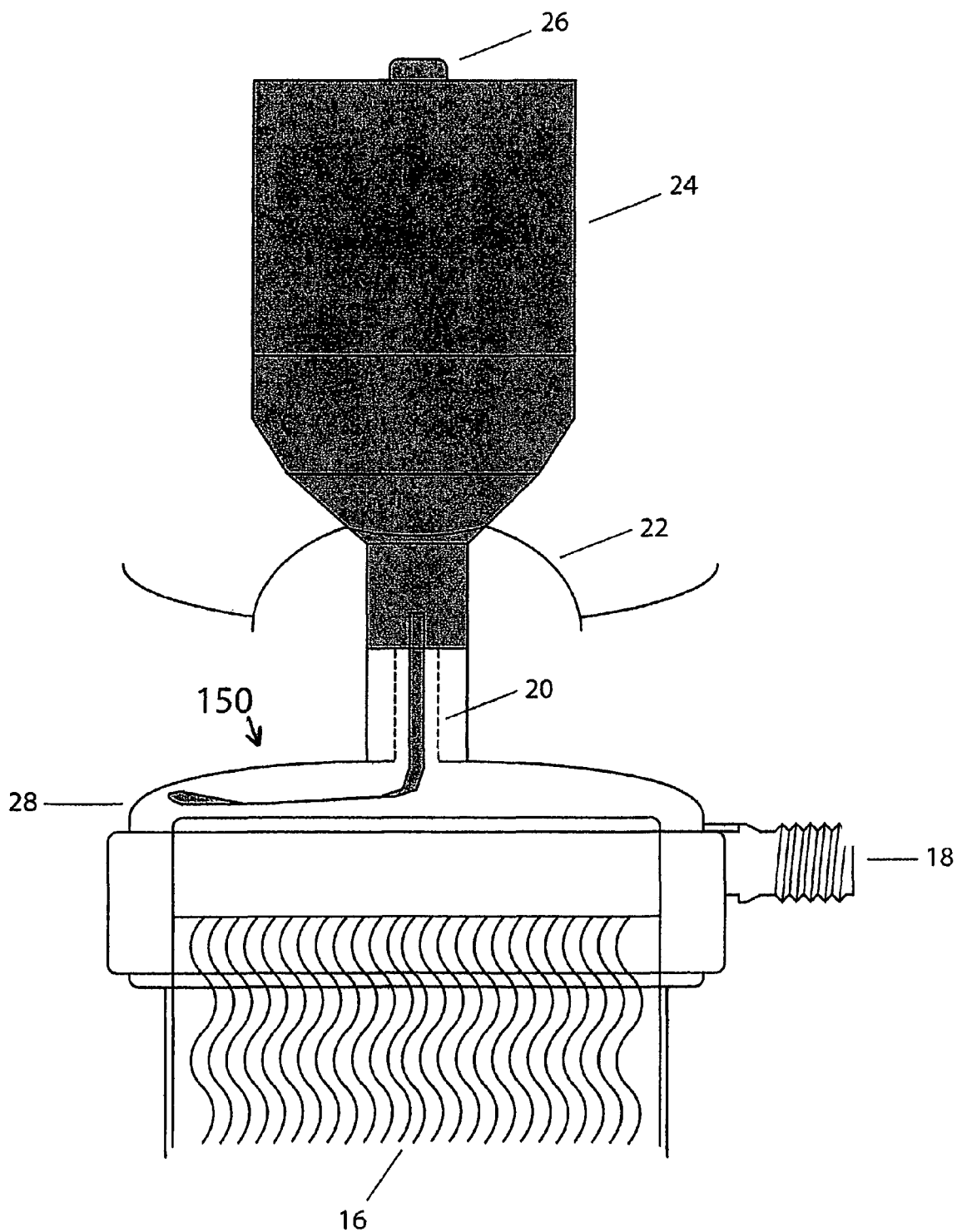
FIG. 2 is a schematic of a handheld device with an optional splash guard and with an insertion device in the header of a dialyzer.
Figure 3:
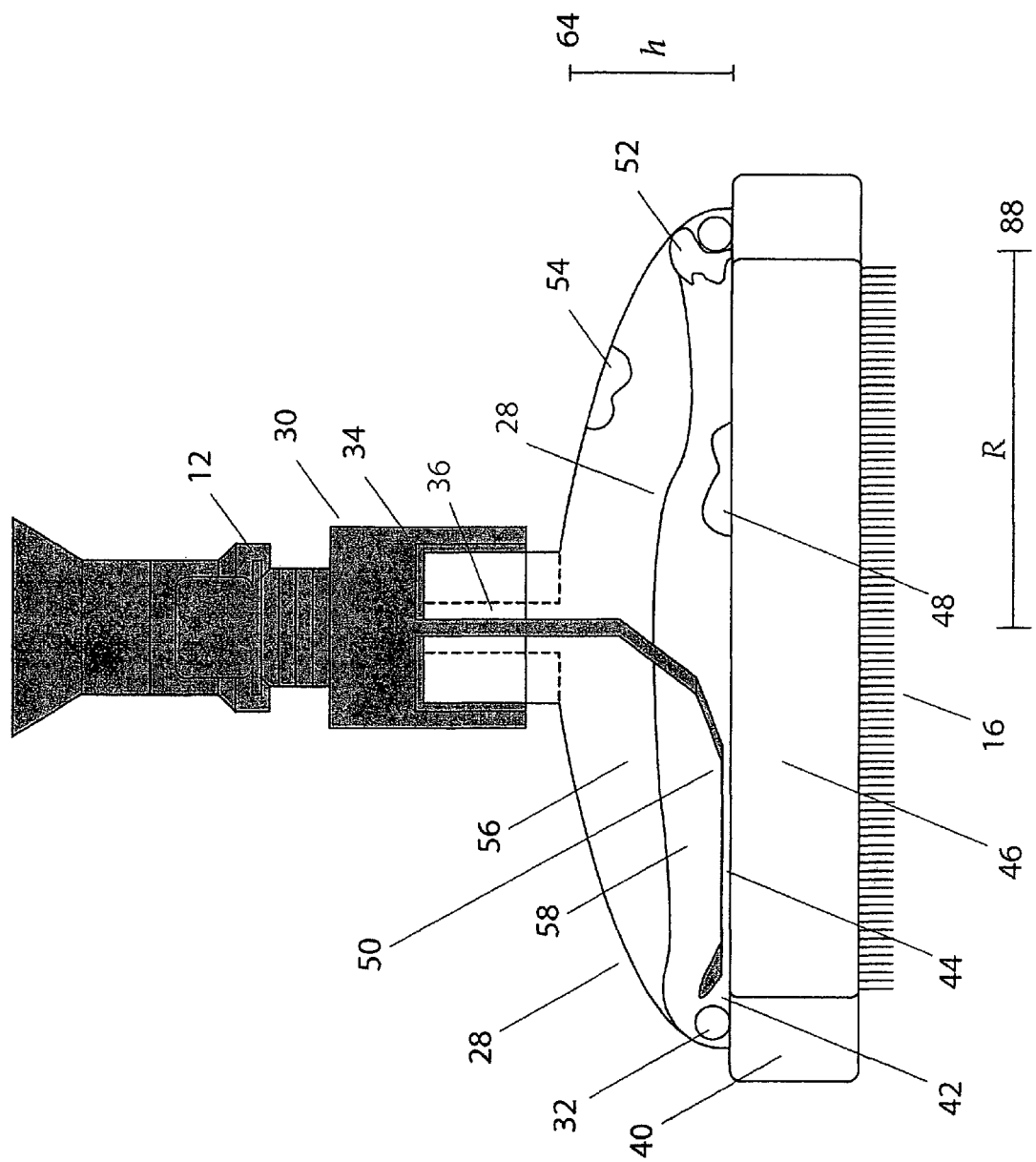
FIG. 3 is a schematic of an insertion device and blood clots or other debris in a header of a dialyzer.

While this invention can clean easily accessible surfaces, it also offers a distinctive advantage of being able to modify (e.g., clean) poorly accessible areas such as the internal cavity 28 shown in FIGS. 2-3. As long as the ID can be introduced into the cavity area and can maintain a small consistent gap over the surface to be cleaned as it moves, other parameters can usually be determined to maximize performance as detailed in the present invention. Some non-exclusive examples include dialyzer header space, channels of endoscopes, air/water channels of flexible endoscopes, the interior of a rigid endoscope and arthroscopes, components of devices and manufacturing process equipment, including filling ports and the like. When cleaning an open surface, a special cavity or space may be created where it is possible to generate the flow fields necessary for cleaning and surface modification with the aid of a movable member, as detailed in the present invention. An example of such arrangement is the use of the methods of the present invention to clean the surfaces of equipment used in the pharmaceutical, biopharmaceutical, food and beverage industries. In this case, the devices and methods will be used to quantitatively transfer adhering and adsorbed materials from the surface to the liquid subjected to flow fields and mechanical action, according to the present invention. Such methods can be used for cleaning validation purposes and in sampling surfaces contaminated with chemical or biological agents, such as in the case bioterrorism or production processes.

While surface cleaning is a major application of this invention, other surface modifications such as coating, disinfection, sterilization, surface and bulk chemical reactions and bulk modification are envisioned. For example, coatings can be smoothed in place in a reversed spin coat application. Coatings can also be textured (e.g., inducing wavelets in a drying solution cast polymer coating), thinned, set at a different rate, forced into fissures, or forced up side walls. An example of bulk modification can be the breaking up of contaminants from the surface and their homogenization to facilitate removal and to minimize re-precipitation of the contaminants. In the following sections, a description of the various components of some cavity spaces are provided to illustrate the scope of the invention. The provided details use a dialyzer header as an example since it represents one clear, instant application of the methods and devices of the invention. However, the general construct of the invention should not be viewed in this narrow context since the fluid dynamics and modes of generating shear stress are applicable to a wide range of cavities, spaces and even open surfaces. The use of an ID to create flow fields and apply shear stresses to surfaces requires similar or derived arrangements based on the description given hereafter.

Access Port

Figure 4:
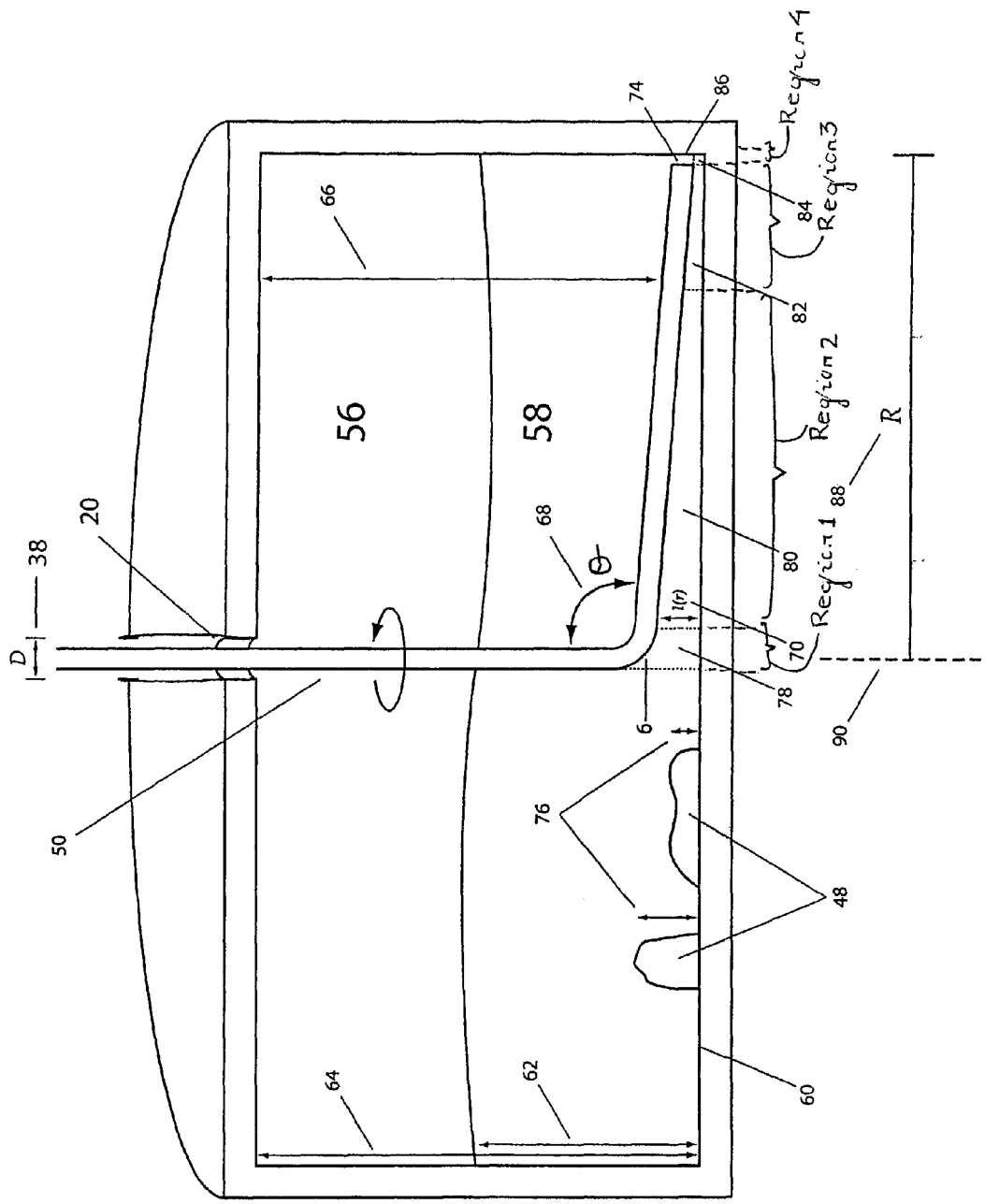
FIG. 4 is a schematic of an insertion device in a cutaway view of a chamber with debris to be cleaned by the insertion device and showing the four fluid dynamics regions.

The access port is preferably a passage through which the ID or movable member/element passes from the rotor to the internal cavity or space to access the surfaces to be cleaned or modified. In the dialyzer header application, as shown in FIGS. 2 and 4, the access port 20 is preferably as centered as possible in the header cap, and part of the ID becomes parallel to the surface to be cleaned. A dialysate part is shown at reference number 18. In another embodiment, the rotor is at least partially in the internal cavity during cleaning or surface modification. In one embodiment, several access ports are positioned so as to overlap several cleaning surfaces. The latter is applicable for larger surfaces and when one or more IDs may be used in the process.

The access port has large enough dimensions throughout its profile to allow entry and motion (e.g., rotation) of the ID. The ID is normally designed to allow easy insertion and removal through the access port. In an embodiment where there is only one access port, there is also enough space in the access port to allow removal of contaminants. Preferably, contaminant removal can occur while the ID is still in the access port. In another embodiment, contaminants are removed through another passageway into the interior cavity. Means of contaminant removal for the case of dialyzer are detailed in this invention.

The access port 20 can be referred to as a neck. In the case of a hemodialyzer, the access port can be referred to as the blood port.

In an embodiment where the ID rotates in the access port, the minimum diameter of the access port is larger than the maximum diameter of the ID to avoid abrasion of the ID surface or the access port interior walls. While straight access ports are preferred to minimize abrasion and for ease of ID insertion, access ports with curves or other longitudinal profiles are envisioned. In one embodiment, an ID sleeve/guide helps ID insertion through these nonlinear profiles.

Insertion Device (ID)

The insertion device (ID) is an at least partially flexible solid shape that can be optionally introduced into an internal cavity to access the surfaces to be cleaned or modified, sweep over a surface to be cleaned, create turbulence and flow fields, and generate mechanical stresses inside the gap with the surface as it moves in at least part of an internal cavity, and optionally can homogenize at least part of the materials or contaminants removed from the surface to be cleaned or modified. FIG. 1a shows an embodiment with a modified monofilament ID 50 with a rounded tip 2, an end portion 4, a flexible shaft 8, and an attachment end 10. Preferably one ID is used at once in a single application. In one embodiment, the ID is inserted in steps to clean several surfaces. In one embodiment, a single ID is splayed into several ID end portions.

In one embodiment an optimal ID length is 6 to 10 cm. In one embodiment, an optimal ID diameter for the part of the ID that is inserted through an opening is within 2 to 3 mm.

ID Surface

The ID preferably has a smooth surface with no protrusions or embedded particulates/fillers that could scratch the surface to be cleaned, change or alter the gap thickness during motion, or disrupt the fluid dynamics or the flow fields optimal to cleaning the cavity under consideration.

In one embodiment the ID has, at least partially, a fin, a soft brush surface (e.g., such as that used in endoscope cleaning), or a coil. In one embodiment, these modifications could modify the ID/fluid interface in a part of the cavity space, modify the Reynolds number, increase homogenization, and cause vibrations in the surface to be cleaned.

ID Length

The ID is preferably long enough to access the area to be cleaned, yet short enough so that the ID tip does not damage any peripheral surfaces during rotation. Surprisingly, the ID length is usually not equal to the radius of the surface to be cleaned. The ID may stretch during movement and may shorten due to drag-induced bending. Depending on the application, the ID material and shape can be chosen to maximize performance. In one embodiment, the ID length can be varied to make up for variations in the surface to be cleaned or in neighboring walls, as in the case of dialyzer header. In one embodiment the ID is marked (on the shaft that connects to the rotor, not at the insertion end) at different lengths to show different insertion lengths for different applications (e.g., for cleaning the header of different dialyzer types or models).

Bends in ID Design

For embodiments where the surface to be cleaned is at an angle α from the axis of rotation, the ID should be able to bend so as to maximize the area swept by the ID. The shaft 8 is flexible enough to enter the internal cavity and partially bend against the surface to be cleaned. However, the shaft also has to be rigid enough to avoid excessive vibrations or harmonics during sweeps over the surface to be cleaned, and to maintain a narrow and uniform gap with the surface to be cleaned. The end portion of ID 4 is preferably modified to increase turbulence in the peripheral region while protecting the surfaces to be cleaned. FIG. 1a shows one embodiment where the end portion 4 is bent.

Figure 1B:
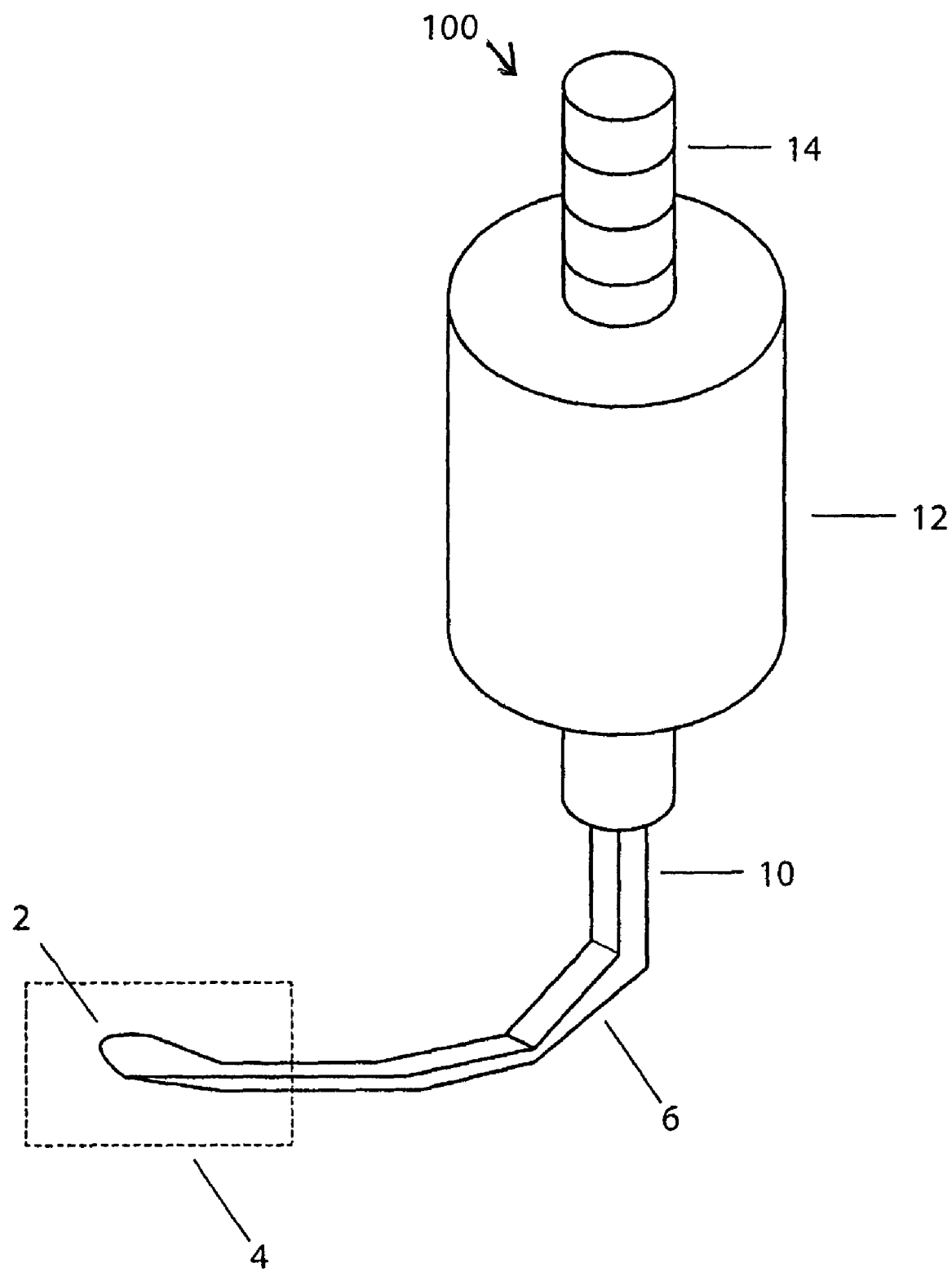
FIG. 1*b* is a schematic of an insertion device with a connector and a rotor.

FIG. 1b shows an embodiment where the ID 100 is kinked, bent, kinked or bent, or formed in a nonlinear shape at predetermined bend areas 6 (bent is defined as bent or bendable by any technique). This allows the ID flexibility to be determined by criteria other than insertion.

ID Longitudinal Shape

FIG. 1b also shows an embodiment where the cross-sectional profile of the ID changes over the length of the ID. In one embodiment, the material or properties of the ID can change along the length of the ID together with a constant or changing cross-sectional profile. FIG. 1b shows one embodiment where the end portion 4 is bulbous.

ID Cross-Sectional Profile

The shape of the rotating ID cross-section enhances the cleaning quality that can be achieved. For example, a larger profile opposing the direction of rotation will sweep a larger volume of liquid. The ID cross-sectional profile is optimal when it creates convergent and divergent flows as it moves over the contaminated surfaces such that effective shear stress is generated to clean the surface and achieve contaminant displacement as it moves out of the surface.

The ID profile is preferably circular or elliptical where surface damage or breakage is of concern, and where minimum gap can be created with the surface to be cleaned. Circular geometry may also be useful to facilitate the conditions of convergent and divergent flow field as the ID moves/rotates within the cavity. In this embodiment, the tip 2 is also rounded or without sharp edges. The profile can change over the length of the ID. In one embodiment, the profile has a larger area near the attachment end 10, and a smaller area in sections of the ID that are designed to be near the surface to be cleaned. In other embodiments, the ID may be rectangular to create the shear and mechanical stresses as for when cleaning high L/D cylindrical channels, as in the case of endoscopes and the like.

While hollow IDs are possible in order to introduce liquids, remove contaminants, introduce vibrations through pulsed pressurized liquid or gas, ID stiffness usually suffers. Solid IDs are preferred embodiments.

In one embodiment, at least part of the ID cross-section is designed for ease of insertion into the access port (e.g., the header of the dialyzer) of the internal cavity, which then creates an approximately 90° angle between the access port axis and the surface to be cleaned (e.g., puttied surface of the dialyzer header region). In this embodiment, an asymmetric cross-section facilitates bending while maintaining stiffness. For example, a rectangular cross-section would be preferable over a circular cross-section by allowing a more rigid ID material. An ID with a rectangular cross-section has one side much larger than its second side to easily bend in the axial direction and to resist azimuthal bending. The larger side is also smaller than the smallest internal diameter of the access port. The gap between the ID and the internal wall of the access port or protector sleeve is preferably small enough to restrict the position of the axis of rotation. Triangles, airfoils, and other asymmetrical cross-sections are also envisioned as part of this invention.

ID End Portion

In many cases, cleaning the bottom surface of a cavity space is not the only area of concern; and the peripheral walls of the cavity must also be cleaned. In these cases, the end portion and tip of the ID need to be considered to effectively clean the walls of a cavity. The ID's end portion 4 is preferably different from the rest of the ID. In certain embodiments, the end portion is bent so that it sweeps forward or backward during movement over the surface to be cleaned. In another embodiment, the end portion 4 is bulbous in two dimensions (e.g., paddle) or three dimensions (e.g., melted end, teardrop, sphere, ellipsoid).

Flexibility is low enough for a given length so that the section of the ID is approximately parallel to the surface to be cleaned such that a small and uniform narrow gap/distance is maintained during the motion of the ID. Distortion or wobbling of the ID should be avoided and this can be achieved by materials selection and by the thickness of the ID. In one embodiment, the ID is flexible at least along part of its length to lie over much of the radius of the area to be cleaned, as in the case of cleaning dialyzer header or similar shaped cavities. In another embodiment, the ID is bent or kinked at a predetermined point 6 along the ID to ensure better preliminary alignment with the surface to be cleaned. In one embodiment, the ID end portion can also be thinner than the remainder of the ID to increase its flexibility.

ID Tip

The design of the ID tip is important in cleaning the end section or peripheral walls of the cavity space, as in the case of dialyzer header. Proper ID tip shape increases localized turbulence to sweep contaminants from the surface and create special flow fields depending on the geometry of the cavity to be cleaned, and optionally into the path of the ID. In an embodiment for cleaning a vertical wall, the ID tip would be shaped in a complementary vertical profile to provide a uniform and minimal gap within the entire gap surface in a vertical direction. For example, a vertical profile at the ID tip will cause more shear and turbulence at the periphery of dialyzer headers.

The ID tip can also be designed to minimize fraying or other damage to the ID. Further, the ID tip can also be weighted to affect the profile of the moving ID along the surface to be cleaned. A splayed or brush-like ID tip can increase turbulence at low speeds or increase viscous drag in the fluid flow field generated during rotation. The ID tip can also be rounded to facilitate insertion and prevent scratching.

Connection of ID to Rotor

As shown in FIG. 1b, the ID with a rotor or other moving member is shown at reference number 100. The attachment portion of the ID 10 can be attached to, and detached from, a rotor or other moving member 14 by a connection 12. Preferably, the connection 12 is a quick connect coupling that connects the attachment end to the moving member 14. For example, there can be a quick connect on the ID, the rotor, both, or between the ID and the rotor. In one embodiment, the connection 12 also maintains the position of the ID relative to the surface to be cleaned perpendicular to the surface to maintain spacing between the ID and the surface to be cleaned, and to maintain a symmetrical cleaning area. For example, FIG. 3 shows that a rotatable screw cap 30 attached to the connection could screw onto the body containing the internal cavity, such as the case of dialyzer header. Some non-exclusive examples of connections can include threads, a chuck, a quick connect (e.g., like a pipette tip), a friction sleeve, a non-circular profile to resist rotation, and others.

Splash Protection/Guard

Movement of the ID may cause liquids like blood and contaminants to splash or spatter through the access port or other opening. One embodiment of the present invention also has a splash protection/guard. Some non-exclusive examples of splash protection are a guard, a shield, an absorbent, or combinations thereof. FIG. 2 shows one example of a splash guard 22. Splash protection contains or deflects liquid and contaminants from the internal cavity while preferably allowing gases to access the internal cavity. The rotatable screw cap 30 in FIG. 3 may be used with splash protection or may replace splash protection, especially when gas access is not necessary. In one embodiment, splash protection can be screwed onto a dialyzer or other entity to be cleaned. In one embodiment, the splash protection is flexible. Some non-exclusive materials for shields can include silicone, and other polymers or metals. Some non-exclusive materials for absorbent protection can include cotton, absorbent nonwovens, sponges, and the like.

Sleeve

In one embodiment, a protector sleeve temporarily covers all or preferably part of the ID. This sleeve could protect the ID from damage and possible contamination. In another embodiment, a preferably tubular protector sleeve temporarily straightens an ID with a bend or kink by covering the bend or kink 6 so that the ID is more easily inserted into a cavity to be cleaned. Preferably, the protector sleeve can fit into at least part of the entry to the cavity. In another embodiment, the protector sleeve can have a distal profile and a cross-profile designed to aid the ID to enter a narrow, high-aspect-ratio, or a non-linear entrance into a cavity to be cleaned. In another embodiment, a stiff bent sleeve (e.g., stainless steel) can position a monofilament ID that is fed or retracted through the interior of the sleeve towards the periphery of the surface to be cleaned.

ID Uses

In a preferred embodiment, the IDs are disposable after a single use. This can avoid cross-contamination or ID degradation. In another embodiment, the ID can be sterilized or aseptically processed (e.g., with peracetic acid). Other means of sterilizing the ID are possible, including steam dry heat, ETO, and exposure to plasma or radiation. Dialyzer or hollow fiber membrane module headers are examples of this application.

The ID is preferably inserted only when needed. However, it is also envisioned in the scope of the invention that the ID is repositioned in the cavity to be cleaned and rotated when necessary. For example, dead zones around sensors and access ports of in-line processes could be periodically cleaned without opening the system. A magnetic or other type of sealed rotating shaft could connect the ID and the motor or quick connect. The rotation can be induced by direct mechanical engagement with a motor with the aid of contactless means such as the use of magnetic field or the like. The application and cavity geometry dictate the mode and means of inducing the rotation or other sweeping action needed.

ID Properties

The following ID properties are important for maximizing performance.

Flexibility

The ID especially needs to properly sweep a surface, create a uniform spacing/gap with the surface to be cleaned and maintain the fluid dynamics flow field needed for achieving optimal cleaning of the cavity. These properties may be selected according to the flexibility, stiffness, modulus of rigidity, or elasticity of the ID. These can be affected by temperature, moisture content, molecular weight, orientation of molecules, rate of stress, duration of stress, and geometry. For example, there are several standard models for how materials respond to stress, as follows: 1) Elastic—a material has a rest shape and its shape departs away from the rest shape due to stress. The amount of departure from rest shape is called strain, the departure itself is called deformation. The resistance to deformation is called Young's Modulus. A spring obeying Hooke's law is a one-dimensional linear version of a general elastic body. 2) Viscous—a material has no rest shape, but its velocity depends on the applied forces. A dashpot (a shock absorber) is a one-dimensional version of a viscous material. 3) Viscoelastic—a material that is elastic, but also has damping. 4) Plastic—a material that, when the stress exceeds a threshold, changes its rest shape in response. The material commonly known as "plastic" is named after this property.

Strong bending of the ID in the azimuthal direction is less preferable because ID length decreases in the radial direction, as in the dialyzer header application. This decrease leads to the formation of a ring with diameter about R (FIGS. 3-4), where the rotating ID is absent and the cleaning is not provided. For certain cross-sectional profiles, tortional modulus also can become important to minimize rolling of the ID.

For polymer ID applications with hot water or other elevated temperatures, the $T_g$ should be higher than the maximum local cleaning temperature. Materials other than polymers, including metals or ceramic, may be used in some applications as long as they satisfy the fluid dynamic requirements for cleaning or surface modification.

Soft/Tough

The ID used to clean the surfaces of internal cavities should be soft enough to avoid damage to the internal cavity (e.g., hollow fibers, potting compound, or other parts of a dialyzer), yet be tough enough to avoid breakage of the ID itself. However, the ID should not be very soft because during ID rotation the arising hydrodynamic resistance can cause a momentum directed opposite to the ID rotation which can bend the ID in the azimuthal direction. In one embodiment, the ID is softer (low hardness) than any surface it may come into contact with to avoid abrasion of those surfaces. It is particularly important in medical applications to avoid the formation of particulates since they may cause harm to a patient in many ways, including traveling in the blood stream as in the case of dialysis, for example.

Failure/Yield Strength

The ID should not chip, produce particles, or otherwise break apart during normal use. Therefore, IDs should have high tensile strength, tear strength, and hardness tear strength (N/mm) high enough to avoid such complications.

Chemical Resistance

IDs should be resistant to chemicals that they may normally come into contact with. Some typical examples in many embodiments are tabulated in Spartan Scientific Solenoid Value and Air Accessories Catalog, A56-1062, Spartan Scientific, Boardman, Ohio (May 2002).

ID Material

The primary consideration here is selecting a material with a rigidity matched for the ID length and speed so as to maintain proper and stable gaps from the surfaces to be cleaned. Other considerations for some embodiments are the ability to insert the ID through an access port, bend the ID so as to position part of the ID against the surface to be cleaned, mechanical resistance, chemical resistance, etc.

For applications where contamination is problematic, the ID should not be made of materials that are prone to localized failure. Some non-exclusive examples to be avoided are mica-filled or particulate-filled polymers, fiberglass-reinforced polymers, and other composites. Fragile/brittle materials that tend to break off during application, such as glass fibers and ceramics, are also to be avoided in these contamination sensitive applications.

The ID may be coated or otherwise surface treated. Some non-exclusive coating examples include biocide, wetting agent (e.g., polyvinyl chloride), lubricant, moisture indicator, temperature indicator, pH indicator, use indicators, and others. The ID may be coated with or incorporate a controlled release substance (e.g., acid, base, surfactant, flexibility modifier, etc.). Some non-exclusive surface treatments include surface roughening, scoring, polishing, impregnation, and other geometries to fit the intended application. In one embodiment, a laser, and optionally an optical sensor, is attached to a polymer fiber optic ID. Alternatively, a conducting ID can be used for electrodischarge machining or sensing with an optional electronic or electrochemical sensor. Imparting hydrophobicity to the surface of the ID is important for the case of the dialyzer header to avoid attachment of blood or other components as the ID is removed from the header space. This is needed to avoid splashing and to ensure a worker's safety.

Depending on the embodiment, a non-exclusive list of ID material categories and examples can include one or more of the following:

polyvinyl chloride (PVC, e.g., Type 1, Grade 1), chlorinated polyvinyl chloride (CPVC, e.g., Type 4, Grade 1), polypropylene (e.g., Type 1);

fluoropolymers (e.g., PVDF (Polyvinyliodene Fluoride), PTFE (Polytetrafluoroethylene), PFA (Perfluoroalkoxy resin), FEP (Fluorinated ethylene propylene);

elastomers (e.g., Buna-N Nitrile Rubber, EPDM (Ethylene Propylene Diene Monomer), VITON® (Vinyliodene Fluoride-Hexafluoropropylene), fluorocarbon, fluorosilicone rubber, KALREZ® & CHEMRAZ® (Perfluoroelastomer), AFLAS® TFE (Tetrafluoroethylene/propy-lene dipolymer);

polymer blend composites;

semiflexible polymers;

coated materials;

polymer coated metal (e.g., FEP coated stainless monofilament); and reinforced material (e.g., fiber reinforced polymer where abrasion can be avoided).

For cleaning dialyzer headers, some preferred materials include: polyolefins (e.g., polyethylene, polypropylene), FEP, PTFE, acrylic, and some less desirable materials could include: silicone, nylon, polycarbonate, filled polymers.

If more than one material is used, physical mixtures, attached members, co-polymers, blends, coatings, and any other combinations are envisioned.

ID Deflection

For an ID which is subjected to a distributed load and has a fixed support at one end, the maximum deflection of the ID ($y_{max}$) is given by:

$$y_{max} = WL^4/8EI \quad (A)$$

where: W is the uniform distributed load; L is the ID length; E is the modulus of elasticity or Young's modulus. It is material's stiffness and is determined by material only; and I is the moment of inertia. It is a constant and is determined by the ID's cross-sectional shape. It is the ID's resistance to bending. For an ID with a rectangular cross-section, the moment of inertia with respect to a line passing through the cross section's centroid is defined as $bh^3/12$ where b is the width of the ID and h is the height of the ID in the direction of loading. For a cross section with a hollow circular structure, the moment of inertia I with respect to a line passing through the cross section's centroid is defined as $\pi/64(D^4-d^4)$, where D is the outer diameter and d is the inner diameter of the hollow circular structure. Deflection can be adjusted so that the ID length will not decrease to an extent that compromises the cleaning of the peripheral region.

ID Motion

The preferred rotational speed of ID is between 1 to 35,000 rpm. The more preferred value is between 100 to 15,000 rpm and even more preferred value is between 5,000 to 20,000 rpm.

Gaps Between the ID and Surface

We have found that smaller values of gap distance l can create larger shear stress and better cleaning. This effect can be combined with larger ID velocity to further enhance cleaning.

A major embodiment of this invention creates enhanced fluid dynamics in small temporary gaps to remove debris from surfaces by overcoming the forces and moments that attach that debris to that surface. The following sections show some of the equations that can model the gaps, resulting fluid dynamics, and effective forces that can be applied to debris on surfaces.

For simplicity, one embodiment defines three general gap regions between the ID's cleaning sections and the surfaces of an internal cavity. These correspond to the bulk gap, main gap, and tip gap, shown in FIG. 4. However, depending on such non-exclusive factors as the shapes of the ID, entry port, internal cavity geometry, surface roughness, and solids present in the internal cavity, other gaps are envisioned. The details given are supported by the figures and illustrations provided.

Bulk Gap

The thickness of the first defined gap, the bulk gap 66 in FIG. 4, which comprises the bulk of the internal cavity, is usually at least 10 times larger than the thicknesses of other gaps described below. Most of the liquid (or gas/liquid mixture) in the bulk gap rotates much slower than a quickly rotating ID. However, a boundary layer forms in the liquid near the disk surface, whose thickness δ does not depend on radius r or azimuthal angle φ. A rough estimate at steady state can be based on the classical theory of hydrodynamics for a rotating liquid initiated by a rotating disk.

Main Gap

The main gap thickness is the distance l between the ID 50 and the main surface to be cleaned 60. In FIG. 4, this value of l can correspond to the main gap distance 70 at region 1 (reference number 78), region 2 (reference number 80), and region 3 (reference number 82). In a dialysis header, this is the distance between the puttied ends of the hollow fibers and the ID that lays against or parallel to this puttied end. The distance l can be zero along parts of the ID when the stationary ID is pressed against the surface to be cleaned. Parts of this gap may be present because of roughness of the surface to be cleaned, a non-smooth ID (e.g., roughness, protrusions), or vibrations or other flexing of the ID. Some of the gap (e.g., due to ID or surface flexing) can depend on time, angular frequency (ω), r, or combinations thereof.

The theoretical gap $l_s(r)$ (in cm) for a straight rigid ID, at a particular radius r (in cm), can be determined by Equation 1:

$$l_s(r) = \frac{(R-r)}{R-R_1} l_s(R_1) \quad (1)$$

where R is the radius of the area to be cleaned, $R_1$ is the radius corresponding to the boundary between zone $r<R_1$ where ID bending is strong, and zone $r>R_1$, where ID is almost straight. For example, a typical dialysis header could have $0<l_s(r)<(0.3$ to $0.25$ cm). The assumption regarding the straight shape of the ID is an oversimplification because the ID is elastic and therefore bends during motion. This bending against or away from the surface to be cleaned means the real $l(r)$ is less than $l_s(r)$ (FIG. 4). Therefore, $l<15$ when $0<r<R$. The difference between $l$ and $l_s$ is essential when $l_s$ is small, namely at large $r$ when $l_s$ is small. Increasing radius $r$ increases velocity and decreases $l$. Consequently, the cleaning quality has to improve with the increasing $r$ due to both increased velocity and decreased $l$ (e.g., FIG. 4, 82). Correspondingly, separate consideration of the cleaning is necessary close to the axis of rotation (i.e., small r shown at 70 in region 1 (reference number 78 in FIG. 4) with decreased velocity and increased l.

Tip Gap

As a third defined gap, the tip gap 74 (gap thickness at the tip close to the side wall 86 of the cavity, as in FIG. 4) is the difference between R and the radius of the edge to be cleaned (FIG. 4). This tip gap can increase with increased rotational speeds due to bending of the ID, and this will depend on the magnitude of bending.

Hydrodynamic Flow

The two main hydrodynamic flows are inside the main gap between the ID and the surface to be cleaned, and in the bulk liquid in the cavity space. We have discovered that the flow in the main gap plays the major role in the cleaning. Sections of the area to be cleaned (e.g., header bottom where deposits including blood clots are normally present) are mainly cleaned when the rotating ID appears above this section and a thin gap forms between the ID and the section to be cleaned. The cleaning mechanism is much more than merely mechanical.

FIG. 4 shows four regions (Region 1, Region 2, Region 3, and Region 4 (reference number 84)) to illustrate different cleaning mechanisms. The division into four regions, the geometry of the cavity, and the ID shape are for illustration purposes and are not meant to limit the invention. It is possible to have more or less regions depending on the application and geometries used.

The most effective cleaning takes place in Regions 2 and 3. When the height of the contamination of the surface to be cleaned exceeds local $l(r)$, the contamination is able to attach to the ID at the moment of its contact and be involved in the ID movement, leading to contamination detachment. But this occurs within a very narrow vicinity of the ID and where l is very small. At sections closer to the tip of the ID, l tends to be smaller. Consequently, large contaminations with heights of about 10 to 100 μm above the surface to be cleaned can be mechanically removed by the rotating ID, while the thinner contaminations will tend to remain on the surface. This is generally not acceptable for critical cleaning of articles such as the dialyzer header. A layer of blood clots on the bulk thickness will remain in the header causing blockage of hollow fibers and failure of the dialyzer.

Thin or otherwise smaller contamination and non-soluble particles are more difficult to remove than similar larger particles. Since particles that protrude less than about 10 μm from the surface to be cleaned are unlikely to be mechanically removed, this invention uses a hydrodynamic detaching force to remove them. In one embodiment, most contamination with 0.1 to 10 μm heights from the surface to be cleaned is removed by a hydrodynamic detaching force.

This cleaning caused by the rotating ID can be theoretically quantified if the contaminant dimensions and adhesion strength are known. The detachment mainly occurs by shear stress due to the viscous force of liquid moved by the ID. The shear stress may be calculated if the velocity distribution is known.

The creeping flow in the gap produces excessive hydrodynamic pressure within the gap, which creates an upward force (lift force) opposite to the axial force applied to the ID. This hydrodynamic pressure increases l, decreases friction, and reduces attrition. Both the frictional force and the pressure in the gap increase with the increasing velocity. This combination reduces friction within a broad range of rotating velocity.

For a symmetrical cylindrical ID surface, the velocity of fluid in the gap is determined by the local ID velocity $V_\phi(z)$ with respect to an immobile surface (MCS). For this configuration, velocity distribution $V(x,z)$ in the gap and shear stress ($\tau$) on the surface (MCS) can be calculated assuming a cylinder of diameter d and radius of curvature $d/2$ and a z axis ($z=R-r$) parallel to the surface (MCS). The x axis is perpendicular to the surface (MCS), parallel to an ID cross-section, perpendicular to the ID length and has $x=0$ at the surface (MCS). The minimal gap $l_o$ is along the x axis. With the increasing z, $l(z)$ increases and the stress on the surface to be cleaned decreases. Within the gap, $l_o<l(z)<d/2$.

The stress $\tau$ can then be approximated from Equation 2:

$$\eta \frac{2V}{d} < \tau(z) < \eta \frac{V}{l_o} \qquad (2)$$

The difference between these maximal and minimal stress values is very large. Correspondingly, the best condition for cleaning arises near $z=0$, where l is minimal.

Hydrodynamic flow can be laminar at small Reynolds number (Re), turbulent at large Re, or be in a transition or intermediate mode. The Reynolds number for Regions 2 and 3 can be approximated by Equations 3 and 4:

$$Re = \frac{hU_\varphi}{\nu} \sim \frac{0.54 \cdot 2\pi rfh}{\nu} \qquad (3)$$

$$Re = \frac{HV_\varphi}{\nu} = \frac{Hr\omega}{\nu} \qquad (4)$$

where $H=l$ within the gap and $H=h_c$ for the liquid stream flow outside the gap. Assuming an $h_c \approx 3$ mm for water, $10^{-2}$ cm$<l<10^{-3}$ cm, $r \sim R=2$ cm, and $f=20$ Hz, then $2<Re(l)<20$.

Laminar creeping flow is possible at Re $>1$. For example, laminar flow can be preserved within a cylindrical capillary at Re $<800$. The convergent flow (i.e., as the gap narrows in the convergent section of the gap) hampers the onset of the turbulization, while the divergent flow (i.e., as the gap widens in the divergent section of the gap) initiates turbulization. At least within the convergent section of the gap and up to the minimal gap distance $l_o$, the laminar flow is preserved and estimated by Equation 2.

Embodiment Showing Flow Characteristics within the Bulk Gap and Four General Regions Bulk The rotating ID can be approximated by equations from the well-studied rotating disk in a liquid. A boundary layer forms in the liquid near the disk surface, whose thickness $\delta$ does not depend on radius r or azimuthal angle $\phi$. The force balance of the entire shear stress on the surface of the rotating disk plus the entire shear stress on the surface of the immobile disk equals zero. The physical sense is clear. Due to disk rotation, the liquid rotates. But its rotation causes the shear stress on the surface of the immobile disk, which restricts the frequency of the liquid rotation. The absolute value of the entire stress, which retards the liquid rotation, equals the entire stress, which involves the liquid in rotation. An equivalent condition is: the frequency of steady rotation provides a zero total stress, characterizing its interaction with the surfaces. In one embodiment, $\tau_o$ is in the range of 3 to 30 Pascal (Pa). The local viscous stresses can be approximated by Equation 5:

$$\tau_v = \eta \frac{v(r)}{\delta(v)} \text{ and } \tau_u = \eta \frac{u(r)}{\delta(u)} \qquad (5)$$

where $\delta(v)$ is the average hydrodynamic boundary layer thickness on the ID surface, $\delta(u)$ is the average hydrodynamic boundary layer thickness on the surface to be cleaned, v is the azimuthal velocity of the ID, u is the azimuthal velocity of the rotating liquid, and r is the at radius.

The azimuthal velocity of the liquid can be approximated by Equation 6:

$$u \sim v\left(\frac{b}{2\pi R}\right)^{2/3} \qquad (6)$$

where u is the velocity of the liquid in bulk and b is ID thickness.

The smaller frequency of liquid rotation $f(u) \approx 0.06f$ means that the viscous stress on the bottom caused by the main rotating stream is very small in comparison with the stress arising in the gap between the ID and the bottom. This is significant since cleaning will be mostly due to the stresses arising in the gap between the ID and surface to be cleaned. Equation 6 includes the relationship between bulk liquid velocity and ID velocity, and defines the importance of ID thickness (b) and radius (R) on such processes.

Region 1

The flow within the gap surrounding the rotation axes, i.e., where $r<R_1$ defines this region. The rotation ID occupies an essential portion of Region 1. This indicates that the liquid rotation frequency in this zone is not small in comparison with f, and that its azimuthal velocity distribution is similar to that of the rotating ID. As a crude approximation, Equation 7 can be used to estimate the boundary layer thickness at $R_1 \sim 0.5$ cm, $f=20$ sec$^{-1}$, that yields $\delta_o \sim 190$ micron.

The boundary layer thickness where the ID sweeps near the housing can be approximated by Equation 7 (Schultz-Grunow, F., Zeitschr.f. Angew, Math.u.Mech., 15(4):191 (1935)) where $X=(1-r/B)$ and B is housing radius:

$$\delta_o = \sqrt{\frac{v}{\omega^*}} X^{1/4}[4.38 - 5.845X + 4X^2 - 4.46X^3 - 1.29X^4] \qquad (7)$$

The values of X and $\delta_o$ are smaller at larger r values. The boundary layer thickness decreases with the increasing velocity, which in turn increases with the increasing r. The dependence of boundary layer thickness on frequency can be seen, for example, at $X=0.5$ and $v \sim 10^{-2}$ cm$^2$/sec (i.e., for water) to give a $\delta_o$ of 275 μm at 10 sec$^{-1}$ and a $\delta_o$ of 87 μm at 100 sec$^{-1}$.

Accordingly, this yields for the shear stress $\tau \sim \eta 2\pi R_1 f/\delta_o \approx 3.3$ Pa. With the decreasing r, the shear stress decreases very rapidly because, first, the angular velocity decreases proportional to r, and second, the boundary layer thickness increases rapidly as r approaches zero. An estimate of radial dependence for shear stress is difficult because of the divergence of Equation 7.

Typical shear stresses for each region at frequency 20 sec$^{-1}$ are: 3 Pa for Region 1, 3 to 30 Pa for Region 2, 30 Pa for Region 3, and 10 to 30 Pa for Region 4. Therefore, cleaning in Region 1 is the lowest among the four Regions and may need to be supplemented by other cleaning means for the case of dialyzer header, as will be disclosed in the examples below. The magnitude of shear stresses in the other three regions is high enough to remove highly adhering contaminants such as blood clots, deposited protein and biofilm. Hubbe, "Theory of Detachment of Colloidal Particles From Flat Surfaces Exposed to Flow," Colloids and Surfaces, 12:151-178 (1984).

Region 2. Different mechanisms of shear stress formation take place at the boundaries of Region 2, i.e., at $R_1$ and $R_2$. At $R_1$, the velocity distribution near the surface is determined by the liquid rotation similar to the solid body rotation, that is, the induced motion of the bulk liquid itself as it moves as a single solid body. At $R_2$ the gap between the ID and the surface is rather narrow and a separate velocity distribution forms within this gap; this determines the shear stress generated in the gap region during the ID rotation. This velocity distribution will be quantified for Region 3, i.e., for $r>R_2$. In particular, this yields an estimate for shear stress at $R_2$. Hence, within Region 2

$$\tau(R_1) < \tau < \tau(R_2) \qquad (8)$$

where for larger values, an estimate will be obtained later.

From the technological point of view, this estimate is sufficient, while no theory is known for hydrodynamics when the influences of local velocity distribution in the gap and the velocity distribution outside the gap have comparable values. In this case, most of the cleaning is due to the shear stresses generated within the gap between the ID and the surface to be cleaned. The motion of bulk liquid outside the gap will have lower velocity and lower shear stress.

Region 2 (FIG. 4) can be better modeled by application of the boundary layer theory because Re is large in this region. However, this is a special and very difficult task. For practical purposes, it is sufficient that the shear stress varies within Region 2 between its maximal value within Region 1 (3 Pa) and its value in Region 3 (30 Pa) at frequency about 20 sec$^{-1}$ or 1200 RPM.

If the tip of the rotating cylinder is a hemisphere as in one embodiment, the gap between the cylinder tip (Region 4) and the surface to be cleaned can be modeled by a sphere moving along a plane. The hydrodynamic flow can be quantified in the fluid mechanics as described in Lee, et al., "Motion of a Sphere in the Presence of a Plane Interface. Part 2. An Exact Solution in Bipolar Co-Ordinates," J. Fluid Mech., 98:193-224 (1980), and Lee, et al., "Motion of a Sphere in the Presence of a Plane Interface. Part 1. An Approximate Solution by Generalization of the Method of Lorentz," J. Fluid Mech., 93:705-726 (1979) and used for calculating stresses on contaminants. The analysis shows that this model at small Re yields an equation almost similar to that for the cylinder case in lubrication approximation. This means that shear force about 30 Pa may be provided at f~20 sec$^{-1}$ by the selection of a proper axial force, which causes a minimal gap thickness in Region 4, about 100 micron.

Region 3. When the ID is not rotating (at rest), it can make a point of contact with the main surface to be cleaned (main cleaning surface, MCS) because the ID is pressed by the axial force to the MCS. But when the ID rotates, the hydrodynamic lift force disjoins the ID and MCS from each other. Accordingly, a minimal gap thickness l occurs near the contact point. Region 3 is the vicinity of the contact point. As the gap is very narrow, here Re is about 1 and low Reynolds hydrodynamics Reynolds, "On the Theory of Lubrication and Its Application to Mr. Beauchamp Tower's Experiments, Including Experimental Determination of the Viscosity of Olive Oil," Philosophical Transactions of the Royal Society of London, England, 177:157-234 (1887), Hays, "A Variational Approach to Lubrication Problems and the Solution of the Finite Journal Bearing," J. Basic Eng., 81:13-23 (1959), Targ, "Main Task of Theory for Laminar Flow," Chapter 8, Moscow, (1951), Zukowski, Full Edition, ONTI (1937), Chapligin, Full Edition, Izd. Acad. Nauk (1933) can be applied to quantify the hydrodynamic flow and to calculate the shear stress.

Region 4 is the area just near the ID tip. For example, Region 4 could be, at least in part, the cylindrical wall of a dialysis header, where the flow between it and the ID tip causes viscous stress. Since Region 4 is often a hydrodynamic stagnant region, it is hard to clean by many methods, such as multiphase flow. This makes cleaning by the methods of this invention very important. In one embodiment, largely discussed below, a wall with a cylindrically swept profile immediately surrounds the surface to be cleaned defining the interior cavity's surfaces by a top (e.g., ceiling), a cylindrical wall, and a planar surface to be cleaned.

A small gap thickness within the major portion of the radial section of the ID combined with the large pressure produced due to the convergent flow causes a large hydrodynamic resistance to the ID's rotation. However, a large hydrodynamic force exerted on the rotating ID may also cause excessive azimuthal bending. Conversely, smaller gaps give larger hydrodynamic resistance and larger shear stress within the gap to improve cleaning. These conflicting effects can often be decreased by proper selection of the gap shape. For example, a rectangular ID with its longer side facing the surface to be cleaned enhances the hydrodynamic resistance.

In one embodiment, friction can be further decreased by curving this longer side facing the surface to be cleaned, when l is the minimal gap thickness (FIG. 4). For example, the sweeping part of the ID could have a profile of a half-circle or a rectangle modified to have one longer side curvature or symmetry.

Hydrodynamic conditions within Region 4 are very different from those in Region 3. The ID tip is preferably further designed in order to optimize Region 4 cleaning. Proper ID tip shape can minimize the thickness of the gap between the ID and the cylindrical wall. To maximize cleaning of a vertical wall, the ID tip would be shaped in a complementary vertical profile to provide a uniform and sufficient gap within the entire gap surface in a vertical direction. However, for a dialyzer, the shape of the cylindrical wall near the header bottom is not vertical. To approximate within Region 4, the cylindrical wall can be considered as locally flat with an angle of $\alpha$ between the cylindrical wall and the surface to be cleaned (e.g., header bottom). Hence, the shape of the ID tip should complement (e.g., mirror) the shape of the cylindrical wall within Region 4. The ID tip can be flat in the axial direction with the angle $\theta$ (FIG. 4) to give a thin uniform gap within the entire Region 4. The gap can be lessened by increasing the axial force applied to the ID, lengthening the ID, reducing the rotation speed (i.e., to reduce bending), or any combination thereof. If axial force applied to the ID is increased, the gap between the ID and the cylindrical wall and the gap between the ID and the header bottom usually both decrease. This can increase the risk of attrition and clogging of hollow fiber ends. As mentioned above, the hydrodynamic lift helps to increase the gap between the ID and the bottom in its narrowest section to minimize attrition.

Although cylindrical wall attrition is not as harmful as attrition of hollow fibers, resulting ID tip attrition and shape change can be harmful to a dialyzer. ID tip shape change leads to a non-uniform gap. Broader gap sections will have poorer cleaning. To prevent the tip attrition, the initiation of the hydrodynamic lift (disjoining) force is necessary. Even with the direct contact of the ID tip with the cylindrical wall, with the large applied pressing force this gap will broaden, the direct contact will be eliminated, when rotation velocity will be sufficiently large, due to the arising hydrodynamic lift force. For the enhancement of the useful hydrodynamic lift force, the shape of the ID tip in the azimuthal direction has to be cylindrical (FIG. 4). This causes the convergent inflow of liquid into the gap that is accompanied by the appearance of excessive pressure within the gap with its maximum not far from the location of the minimal gap thickness. The large enhancement of the shear stress near the narrowest section of the gap is favorable for cleaning.

For suppression of the fluctuation of the gap thickness, fluctuation during rotation is an additional condition necessary to optimize Region 4 cleaning. The gap thickness may periodically and temporarily increase to 0.1 to 1 mm. A~1 mm gap thickness may decrease the shear stress by 10 to 100 times (compared to the stress when the gap is <0.01 to 0.1 mm).

There are two reasons for the periodical increase in the gap thickness. A reasonably constant gap thickness requires an ideal cylindrical shape of the "cylindrical" wall. For any azimuthal angle, the diameter of the header in the direction parallel to its bottom has to be invariant. This condition is difficult to accomplish during the fabrication of the housing of a dialyzer. Fluctuation of 0.1 mm to 1 mm in the internal diameter of the 5 cm housing is generally unavoidable. It is obvious that this small variation causes a huge variation in the gap thickness with the cylindrical wall.

To allow rotation, the ID length should not exceed the minimal internal radius of the internal cavity (e.g., header) near its bottom. While the gap thickness is minimal at the angle, corresponding to the minimal internal diameter of the header, the gap thickness increases and reaches the maximal value at an angle $\alpha_o$, corresponding to the maximal internal diameter of the header. At angle $\alpha_o$, the gap thickness is about equal to the difference between the maximal and the minimal diameters of the header (e.g., ~0.1 to 1 mm).

The second reason for the periodical formation of the broader gap is the difference between the geometrical axes of the cylindrical header and the real axes of the ID rotation (eccentricity).

In an embodiment with a rectangular ID with long side b is inserted through a cylindrical access port with inner diameter $D_o$, b has to be smaller than a critical value $b_{cr}$ when there is direct contact between the ID and the internal surface of the access port. The direct contact will cause ID attrition and deformation, which are harmful for its performance. Therefore, the gap between the ID and the internal surface of the exit tube should be $\geq 100$ μm. This gap will fluctuate during ID rotation due to the position of the real axes of rotation. Two cases are exemplified:

Case 1. The fixed position of the axis of the rotor, which rotates the ID, and the fixed position of the dialyzer, should coincide. When the rotor axis position is fixed, there is an unavoidable difference in the axis position for the different dialyzers because the difference in the external diameters of their housings may be about 0.1 to 1 mm. The same periodical variation in the gap between the rotation ID and the cylindrical wall will arise.

Case 2. An additional reason for the fluctuation of the ID axis of rotation is its elasticity. Its bending 90° when it is inserted into the header indicates that it changes its shape, and in particular, the position of its rotation axis under the applied force.

ID deformability, which is necessary for its insertion into the header, indicates how the periodical variability arising from the gap between the ID tip and the cylindrical housing can be prevented. The elasticity modulus of the ID material has to permit its deformation in both axial and azimuthal directions (FIG. 4).

It is obvious that ID deformability in the azimuthal direction will be very small in comparison with that in the axial direction because b>>α. This may not cause a problem because a small deviation in azimuthal direction from the straight shape is sufficient while 90° bending is necessary in the axial direction. The axial pressing force applied to the ID has to be so large so that its radial section deviates from the straight shape and its length increases due to the azimuthal bending. The extra length due to this bending is about 1 mm. Due to the applied large axial force to the ID rotor, the ID tip, during rotation, is pressed to the cylindrical wall despite the fluctuation in the distance from the ID axis to the wall. In the moment when this distance increases, the shape of the radial section of the ID transforms from the bent shape to almost a straight shape, i.e., its length in the radial direction increases. This provides the continuous "touching" of the ID tip to the cylindrical wall despite the distance between the rotation axis and the cylindrical wall changes being an unknown function of the azimuthal angle, which characterizes a momentary direction of the radial section of the ID. If it turns out that the deformation in the azimuthal direction is too small when b>>α, an ID section near its tip can be fabricated with the b/α ratio gradually approaching one (FIG. 4).

An additional condition of the pre-deformation of the ID in the azimuthal direction is that between two possible directions of the ID deviation from the straight shape, the deviation in the direction opposite to the direction of the rotation is necessary. In this case, further increase in this deviation during rotation will be provided.

If the initial deviation of the ID from the straight shape is in the direction of the rotation, its breakage during the rotation is possible. Indeed, in the moment when the ID tip collides with an asperity on the internal cylindrical wall, this collision cannot be damped due to the ID shape deformation because a strong momentary deformation from the concave to convex shape (in the azimuthal direction) is necessary. The momentary transition from the concave to convex shape corresponds to a large azimuthal stress, which will cause either the plastic deformation of the ID or its breakage. The plastic deformation is harmful as well because it corresponds to the permanent large gap between the ID tip and wall.

Note that the colliding of the ID tip with an asperity will not cause its plastic deformation when its initial deviation from the straight shape is oriented opposite to the rotation direction. A small increase in this deviation during the collision is sufficient to continue the rotation. This small increase in the initial deviation may be in the range of the elastic deformations.

It is noteworthy that even a small asperity on the internal cylindrical wall of about 1 to 10 μm may cause a large momentary stress within the ID tip because it is pressed to the wall. The polishing of the external cylindrical wall may remove the asperities, but this is not planned in the dialyzer fabrication.

When the initial ID deformation is provided by the axial loading of the rotor, its deformation is visible through the housing ceiling. Hence, the direction of the rotation has to be chosen taking into account the initial direction of the ID deviation from the straight shape. For this procedure, the ability of the rotor to rotate in both directions has to be available.

Shear Stress Upon Contaminants

We have discovered that as the gap size diminishes, the fluid flow rate increases and can be made to become more laminar, thereby increasing shear stress ($\tau$). We have applied this principle to remove debris or other particles from surfaces by generating a large enough shear stress ($\tau$) to overcome the particle's moment and adhesive forces between the particle and the surface.

Shear stress ($\tau$) can be calculated by Equation 9:

$$\tau = \eta \frac{dU_\varphi}{dZ} = \eta \frac{0.54 \cdot 2\pi rf}{\delta_o} \qquad (9)$$

Lubrication theory can be used to estimate the shear stress in the gap between a rotating cylindrical ID and the surface to be cleaned. In another embodiment, the cylindrical ID moving along a flat surface to be cleaned can be adapted from Reynolds theory for the lubrication between cylinders. The shape of the gap is characterized by Equation 10.

Examples of classical lubrication theory are described in Reynolds O., On the theory of lubrication and its application to Mr. Beauchamp Tower's experiments, including experimental determination of the viscosity of olive oil, Philosophical Transactions of the Royal Society of London, England, 177:157-234, (1886); Hays, D. F., A variational approach to lubrication problems and the solution of the finite journal bearing, J. Basic Eng., 81:13-23, (1959); Cameron, A., Basic Lubrication Theory, 3rd Edition, pp. 37-51, 93-125, John Wiley & Sons, New York, N.Y., (1981); Fuller, D. D., Theory and Practice of Lubrication for Engineers, 2nd Edition, pp. 198-296, John Wiley & Sons, New York, N.Y., (1984); Leal, L. G., Laminar Flow and Convective Transport Processes: Scaling Principles and Asymptotic Analysis, pp. 396-406, Butterworth-Heinemann, Newton, Mass., (1992). Classical Reynolds theory for the lubrication in the gap between two unparallel flat surfaces can be adapted to one embodiment of the present invention.

$$l = l_o\left(1 + K\frac{z}{a}\right) \quad (10)$$

where l is the profile of the gap in the direction of ID rotation.

The stream induced by the local ID velocity V with respect to the MCS causes a pressure drop, even if there is no applied pressure difference. This pressure drop provides a consistent volumetric velocity through any cross-section of the gap. Without a pressure drop, a smaller cross-section creates a smaller volumetric velocity. This is because V is the same along any part of the gap/ID's cross-section. Hence, the pressure gradient decreases the liquid stream volume through the wider part of a gap cross-section due to the inversion of the velocity direction. This occurs near the ID's immobile surface (in the coordinate system of the immobile surface) because the velocity induced by the difference in plane velocities is smaller near the surface. This velocity distribution is described by:

$$V_z = \frac{1}{2\eta} \cdot \frac{\partial P}{\partial z}(x^2 - h(z)x) - \frac{V}{h(z)}(h(z) - x) \quad (11)$$

where z is the distance in the direction of movement, z=0 in the center.

The second term in Equation 11 roughly models Region 3, while the first term demonstrates the significance of the induced pressure drop. Binomial Equation 11 leads to binomial Equation 12 for the shear stress distribution along the gap:

$$\tau = \eta \frac{V}{l_o}\left[\frac{4a}{a + Kz} - \frac{6(1+K)}{2+K} \cdot \frac{a^2}{(a+Kz)^2}\right] \quad (12)$$

where a is the radius of cylindrical ID. At z=0, the difference between Equation 12 and right hand side of Equation 2 is small. By increasing axial force, $l_o$ may be decreased to a small value, for example, 100 micron. This yields $\tau(R_2)\sim 25$ Pa which is sufficient for cleaning blood clots and like contaminants.

Suggested Removal Mechanisms

Contaminants usually adhere to surfaces by chemical, electrostatic, hydrogen bonding, and physical/mechanical (e.g., interlocking) forces. The adhesive force is proportional to the adhering surface area, but may be somewhat counteracted by thick contaminants.

Mechanical overcoming of this adhesion can occur by shear or lateral forces. However, lateral forces usually require transfer of many times as much force as shear forces in order to remove contaminants. In one embodiment, chemicals or liquids help reduce contaminant adhesion to lessen the required shear forces for contaminant removal. Some non-exclusive examples can be introducing a liquid by capillary action into the interface between a contaminant and a surface, or swelling the contaminant (e.g., with a surfactant, solvents or cleaning agents). Chemically-assisted embodiments can use methods such as attacking cross-linking, by modifying the pH of the interface, oxidation, hydrolysis, changing Zeta potential or other electrostatic surface phenomena, NaOH attack and emulsifying fats and lipids, etc. Therefore, the use of cleaning agents or chemicals or physical modification of the adhesion of the contaminants with the surface are necessary in many applications, and can be tailored by those skilled in the art to satisfy the cleaning conditions according to this invention. It is also envisioned that gas can be used to lessen adhesion by drying and entrained bubbles. Higher temperatures often also reduce adhesion, increase the rate of reaction such as hydrolysis or oxidation, and improve the removal of lipids, especially when cleaning temperature is adjusted higher than the melting points of the contaminants. The use of oxidizing agents such as hypochlorite, hydrogen peroxide and peroxy acids is contemplated for removal of blood clots, proteins and other organic contaminants. The use of high or low pH may be required depending on the nature of the contaminant. For example, the removal of inorganic scale such as calcium carbonate and the like is better accomplished with the use of acids such as HCl, or other inorganic acids, or organic acids including citric, glycolic, hydroxacetic and the like. If the adhering contaminants include particles such as silt or cell fragments, the use of dispersants will be required. Applications in separation membrane modules and process equipment comprise the major uses of the present invention.

In order to remove a contaminant, the shear force must be greater than the adhesive force of the contaminants with the surface to be cleaned. Computational fluid dynamics software and fluid-solid interaction multiphysics software (e.g., ANSYS, Inc., Canonsburg, Pa.) can be used to calculate improved fluid dynamics in certain applications.

Blood clots typically adhere by a multitude of forces including electrostatic, covalent, and hydrogen bonding. Overcoming blood clot adhesion on rough polymer surfaces (e.g., fiber ends puttied in polyurethane) requires overcoming interlocking mechanical adhesion and other specific bonding forces.

In previous models, removal of colloidal spherical contaminants from a surface is largely due to the hydrodynamic detaching force overcoming adhesive resistance to rolling Yiantsios, et al., "Detachment of Spherical Microparticles Adhering on Flat Surfaces by Hydrodynamic Forces," J. of Colloid and Interface Sci., 176:74-85 (1995), Ryan, et al., "Colloid Mobilization and Transport in Groundwater," Colloids and Surfaces, 107:1-56 (1996), Hubbe, "Theory of Detachment of Colloidal Particles From Flat Surfaces Exposed to Flow, Colloids and Surfaces," 12:151-178 (1984), Hubbe, "Detachment of Colloidal Hydrous Oxide Spheres From Flat Solids Exposed to Flow 1." Experimental System, Colloids and Surfaces, 16:227-248 (1985), Hubbe, "Detachment of Colloidal Hydrous Oxide Spheres From Flat Solids' Exposed to Flow 2." Mechanism of release, Colloids and Surfaces, 16:249-270 (1985), and Hubbe, "Detachment of Colloidal Hydrous Oxide Spheres From Flat Solids Exposed to Flow 3." Forces of adhesion, Colloids and Surfaces, 25:311-324 (1987). However, in real world applications, it is more accurate to consider that the larger the couple (moment) produced by wall shear stress, the better the detachment and cleaning:

$$T = 8\tau_w d^2 \quad (13)$$

where T is the moment applied to the particle.

The rapid decrease of T with decreasing d, also seen in experiments, shows that smaller contaminants are more difficult to remove. These results are obtained when $d < \delta$. This condition does not cause serious limitations because even small contaminants have to be removed. If smaller contaminants are removed, larger contaminants will also be removed. Hence, the condition of high quality cleaning has to be formulated for small contaminants. Correspondingly, the condition d<δ has to be satisfied. It is interesting to note that the shear stress is much larger than the critical stresses, about 100 dyne/cm², which is sufficient for the removal of adhering contaminants, according to Truskey, et al., "Relationship Between 3T3 Cell Spreading and the Strength of Adhesion on Glass and Silane Surfaces," Biomater, 14(4):243-254 (1993), and Truskey, et al., "The Effect of Fluid Shear Stress Upon Cell Adhesion to Fibronectin-Treated Surfaces," J. Biomed. Mater. Res., 24:1333-1353 (1990).

Process Variables

Many embodiments of the present invention can be affected by external variables. For example, temperature can change viscosity and strength of materials (e.g., 1D), solubilize solids (e.g., salt, scale, residue), increase rates of chemical reaction, increase transport rates, liquefy fat, etc. The ID can be designed in view of these effects or for secondary considerations. For example, a thermally dependent indicator could be incorporated in or on the ID to show use.

Dialyzers Application Combined with Multiphase Cleaning Methods

The application of the two-phase flow cleaning method see U.S. Pat. No. 6,027,572 to Labib, et al., U.S. Pat. No. 6,326,340 to Labib, et al., U.S. Pat. No. 6,454,871 to Labib, et al., U.S. Pat. No. 6,619,302 to Labib, et al., U.S. Pat. No. 6,857,436 to Labib et al., U.S. Publication No. 2004/7255 to Labib, et al., and U.S. Pat. No. 6,945,257 to Tabani, et al., within dialyzer headers can have less effect in the dead periphery regions, where fiber bundle terminates. The horizontal velocity $V_r$ near the axis exceeds very much the velocity $V_f$ inside fibers due to R>>h. Therefore, at each value of r, the condition of the invariant volumetric velocity has to be satisfied:

$$V_f \pi (R^2 - r^2) = 2\pi r h V_r \quad (14)$$

or $$\frac{V_r}{V_f} = \frac{R - r^2}{2rh} >> 1 \quad (15)$$

Smaller values of r give larger velocity within the header, which favors cleaning by the two-phase flow cleaning method. Larger values of r give smaller gaps (l) that correspond to larger shear stress, which favor cleaning by the rotating cylinder. Hence, combining the two-phase flow cleaning method with a rotating ID maximizes header cleaning at any r. Therefore, the two-phase cleaning method will be complementary with the present invention in cleaning Region 1, as described above, and therefore, the combination of the two methods will provide better cleaning results. It should be made clear that the methods and devices of the present invention are quite effective by themselves with respect to cleaning dialyzer header, and they should not be limited for use with the two-phase cleaning method. One skilled in the art would recognize the utility of the present invention in cleaning dialyzer headers prior to the use of automated reprocessing devices such as the Renatron®, Seratronics®, and other similar devices. In addition, the invention is not intended to be limited to dialyzer header cleaning, but to any cavity or constrained space where the combination of fluid dynamics and ID geometries may be tailored or designed to fit various applications. The use of complementary cleaning solutions to facilitate the cleaning process is also contemplated within the scope of the invention.

Device

The ID is preferably moved by a motor via rotor 14. Non-exclusive examples of motors include AC, DC pulsed, chopped AC or DC, electric, air, liquid, constant, variable speed, variable torque, pulsed, partial duty cycle, DREMEL™, and the like. The motors are preferably rotating to create a rotational sweep.

In an alternative embodiment, the motor may create a linear sweep. The term motor is defined to include devices other than traditional motors that are better suited to creating two-dimensional sweeps. Linear sweeps are ideally suited for cleaning between parallel plates such as found in filter plates, heat exchanger fins, and the like.

The rotational speed of the motor must be matched to the angular velocity of the ID tip. While the main result should be generating enough shear stress to remove contaminants, angular velocity also affects damage to surfaces, homogenization of contaminants such as blood clots in the case of the dialyzer or like applications, and emulsification or related processes. It is possible to adjust the rotational speed of the motor to achieve both contaminants detachment and homogenization at the same time, depending on the application. In the case of dialyzer header, homogenization of blood clots is preferred since it facilitates the removal of blood from the header space through a narrow access port. The shear stress needed for contaminant detachment may be the same or different from that required to effect homogenization. Preferred shear stress values ($\tau_o$) applied to contaminants are 10 Pascals to 1,000 Pascals or more, depending on the adhesive strength of the contaminant with the surface to be cleaned. More preferred shear stress includes the range between 20 and 400 Pa.

For an ID cleaning a single circular surface of 5 cm diameter, the maximum rotational speed of the motor is preferably 100 to 2,000 rpm, more preferably 500 to 5,000 rpm. The lower rotational speed has to give enough angular velocity to the ID to generate shear stress. The higher rotational speed has to be low enough so as to avoid damage to the ID or the surface to be cleaned.

The motor and attachment may be mounted permanently on a stand and considered as an independent device, or used as a component of a larger system as in dialyzer reprocessing, other medical devices or process equipment. FIG. 2 shows a motor preferably contained in a housing 24 with a switch 26. In a handheld device, the ID is attached to a handpiece comprising a motor controlled by a switch 26 that is preferably normally off and turned on while pushing the switch, or for a timed period afterwards. In another embodiment, the invention is part of an automated system, attached to a control system, and comprises a mechanical system for inserting and removing the ID.

It is envisioned that the present invention can be used with any dialyzer cleaning machine in the form of a handheld device, and used in either manual or automated modes. In one embodiment, it is envisioned that the manual and automated embodiments can also be combined with a Clearflux HD (Novaflux Technologies, Princeton, N.J.) or Renatron® cleaning system. U.S. Pat. Nos. 6,027,572; 6,326,340; 6,454,871; 6,619,302; 6,857,436; and 6,945,257; and U.S. Patent Application No. 2004/0007255, which are incorporated by reference herein, provide details of the two-phase cleaning method and relevant applications in dialyzer reprocessing and membrane cleaning.

The motor that drives the ID is preferably housed in an easy-to-clean housing (e.g., plastic). The motor's rotor is preferably perpendicular or parallel to the surface to be cleaned. Other angles can cause an unsymmetrical cleaning area and gap thickness. The motor, connection, or ID may be clamped or otherwise held in a constant position relative to the surface to be cleaned. The ID may also be automatically inserted, moved, and removed.

FIG. 4 shows an ID 50 that is rotated around a rotor axis (with a center at R=0) and has a bend 6 of θ degrees from the rotor axis 90. If the access port 20 has a large enough diameter (D) 38, the rotor axis 90 may be off center (R does not equal 0). Also, the surface to be cleaned and the access port do not have to be centered in the internal cavity. θ is preferably 89° to 95°, more preferably 90°. Preferably, at least 90%, more preferably at least 99%, of the bend is in Region 1. The bend angle θ is shown at reference number 68.

The ID 50 preferably sweeps a radius less than but as close as possible to the radius to be cleaned R. The ID 50 physically sweeps a volume=(R-tip gap*a), where "a" is the thickness of the section of the ID 50 that sweeps above the area to be cleaned. In non-symmetrical profiles, "a" usually does not equal the average diameter of the ID. The ID thickness "a" is shown at reference number 72. The tip gap is shown at reference number 74.

Method

The shear stress generated in the gap between the ID and the surface to be cleaned has to be great enough to overcome surface adhesion of contaminants. In one embodiment where a contaminated internal cavity of a device can be accessed through a hole, the ID is inserted through the hole such that part of the ID lies at least approximately parallel to the surface to be cleaned. Then the ID is moved (preferably rotated) across the surface to be cleaned. The ID is accelerated to a high enough angular velocity such that sufficient turbulence sweeps contaminants from the surface to be cleaned even without direct physical contact between the ID and the surface. The angular velocity of the ID needs to be adjusted to generate shear stress in the gap between the ID and surface sufficient to overcome the adhesive strength of the contaminant with such surface. Guidance to compute shear stress in the gap has been provided by the analysis given in the specification. The mathematical equations given need only be used to determine the approximate range of rotation speed and angular velocity for the various applications. However, persons skilled in the art can arrive at necessary conditions for cleaning the gap by experimentation using the parameters and variables defined by the analysis. It is therefore clear that the analysis given in this invention provides only guidance to defining the right conditions for cleaning surfaces of the constrained spaces and cavities and their variants.

In the preferred embodiment, there is enough liquid in the internal cavity to ensure flow around the sweeping ID, and preferably in sufficient volume to also entrain the dislodged contaminants. In one embodiment, the liquid can be, at least in part, in the contaminants. Preferably, the liquid is mainly water, since other liquids can make the contaminants more sticky or contaminate the internal cavity (e.g., in biological systems). Solvents can also stress crack some polymers. Cleaning agents can be added to lower the adhesive strength of contaminants with the surface and to impart other functions as described above. Exemplary cleaning agents include surfactants. In addition to cleaning agents, surface modifiers and reactants can be provided. In situations where chemicals such as cleaning agents, surface modifiers, or reactants are used, it may be desirable to provide a rinsing step for the removal of the chemicals.

Having some gas (e.g., air) in the internal cavity can improve turbulence and overcome contaminant adhesion. The moving ID can entrain gas bubbles in the liquid. In some less preferred embodiments with gaseous fluid dynamics, liquid is not used or is present in small quantities. Much higher ID velocities would be required to generate enough shear force due to the lower density and viscosity of gases.

Pretreatments can also be applied at the beginning of this method, but are usually not required. In one embodiment, the internal cavity is presoaked in water, surfactant solutions, high pH solution, chlorine bleach (hypochlorite) solution, hydrogen peroxide, peroxy acids, and the like to soften and/or swell the contaminants. Such a step may be necessary when the contaminant was left to dry or in the case of high adhesive strength situations.

For cleaning areas below 30 $cm^2$, a maximum rotation speed of 1,000 rpm to 15,000 rpm is preferred. The maximum rotation speed is limited by tool damage, flexing, catching, surface damage, and gap space or its uniformity. For example, in biological systems such as cleaning dialyzers, rotation speeds of non-fragile IDs reduce the presence of non-biological particulates (e.g., polymer, potting compounds).

The ID can also homogenize or emulsify loosened contaminants in many applications, for example, blood clots in the case of cleaning the headers of dialyzers, hemofilters, and other devices where blood is employed or encountered. The sides of the ID that face away from the surface to be cleaned can be designed with a larger or more aggressive profile (e.g., fins) to sweep out a larger area and break up loosened contaminants.

Cleaning times are preferably 5 sec to 1 min, more preferably 5 to 20 sec. Cleaning can be continuous or with a pulse by varying the duty cycle of the motor or the axial pressure to the ID.

After removing the contaminants to the extent necessary, the ID is then pulled out from the internal cavity. The ID can then be optionally cleaned and sterilized, or discarded. In another embodiment, a protective sleeve can be first pushed over part of the ID to straighten it for easier removal. In another embodiment, the ID can be left in the internal cavity and optionally disconnected from the motor. In the embodiments where the ID is removed from the internal cavity, the removal port provides an opening for removal of the contaminants. Otherwise, contaminants are removed around the ID or through some other access to the internal cavity (e.g., as in the main pipe for in-line processes). Dislodged contaminants and blood clots may be removed after the removal of the ID by a subsequent step, or continuously removed during cleaning by providing access for such removal. In the case of dialyzer headers, water or other liquids can be introduced from fiber lumens or by backflushing to flush away dislodged and detached clots or homogenized blood from the dialyzer.

In one embodiment, any of the methods above are used in combination with a two-phase cleaning system such as described by see U.S. Pat. No. 6,027,572 to Labib, et al., U.S. Pat. No. 6,326,340 to Labib, et al., U.S. Pat. No. 6,454,871 to Labib, et al., U.S. Pat. No. 6,619,302 to Labib, et al., U.S. Pat. No. 6,857,436 to Labib et al., U.S. Publication No. 2004/7255 to Labib, et al., and U.S. Pat. No. 6,945,257 to Tabani, et al. In another embodiment, any of the methods above are used in combination with a Renatron®, Seratronics®, or other equivalent devices, or for the cases where manual reprocessing may be practiced.

Dialysis Application

Precleaning dialyzer headers is an ideal application for an embodiment of this invention. However, this application can have some special issues.

As shown in FIGS. 2 and 3, the dialyzer 150 which comprises the dialyzer header cap 28 (typically polycarbonate) with insertion port 36, the potting compound 46 encapsulating the ends of a bundle of hollow fibers 16, and O-ring 32 (in a dialyzer with a removable header cap) defines the dialyzer header 28. FIG. 4 also shows a blood clot 48, liquid 58, gas 56, and ID 50. In FIG. 3, a blood clot at the edge of the header is shown at reference number 52 and a blood clot on the header is shown at reference number 54. Reference number 40 refers to dead space without hollow fiber, reference number 42 refers to the ID edge gap, and reference number 44 refers to the ID surface gap. The height of the liquid at rest in the header is shown at reference number 62, the distance between the top and bottom of the header (h) is shown at reference number 64, and the bulk gap is shown at reference number 66. The clot height is shown at reference number 76. Furthermore, the edge to be cleaned is shown at reference number 86, and the radius of surface to be cleaned (R) is shown at reference number 88.

The dialyzer header cap port connection 34 with threads and insertion port 38 represents either the arterial end or venous end. The arterial or venous sides can be optionally pressurized together with gas, liquid, or mixtures thereof. Either end of the dialyzer can be cleaned individually or simultaneously by this invention.

Contaminants mainly consist of blood clots along with fat deposits, proteins, lipids, fibrous biomass, and other debris. Fat deposits can solidify when cooled (e.g., after refrigeration) and blood clots tend to agglomerate. Blood clots are also highly cross-linked with fibrinogen causing mechanical strength, insolubility and redeposition. Homogenization to minimize redeposition is not possible by spray or solely mechanical means. Fluid dynamics can overcome adhesion, but does not homogenize well. Mechanical action of the ID is the primary homogenizer once contaminants are removed from the surface.

The materials used for the ID or other parts that could contact the dialyzer should have chemical (e.g., PAA, SAA, bleach) and biochemical (e.g., TPA) compatibility with blood, the human body, and materials used in reprocessing. For example, peracetic acid (PAA) and hydrogen peroxide can attack nylon and polycarbonate.

While this invention may be used dry in some embodiments, preferably there is some liquid in the header during at least part of the process. In some embodiments, adding liquid can increase turbulence, increase shear stress, increase particle reduction of contaminants, and reduce ID contact with surfaces. This liquid can come wholly or partially from blood. In a dialyzer application, preferably 40-60 vol %, more preferably 50 vol %, of header is liquid. The preferred volume and ratio of liquid can depend on the size and shape of the internal cavity. In one dialyzer embodiment, there are preferably no additives in the liquid that can cause foaming (e.g., acetic acid), blood contamination, etc. In one embodiment, during the process, additional liquid is added, circulated, or both.

In one embodiment, the liquid is preferably at least mostly water or saline since other liquids can cause the contaminants to become sticky. In one embodiment, saline increases shear in Region 4 and helps clean O-ring regions in dialyzer headers. In one embodiment, pH is increased to reduce contaminant adhesion. Other methods to reduce adhesion can include adding a surfactant. Increasing viscosity of the liquid above that of water can also increase the shear forces.

Preferably, the header is not opened, thereby minimizing cross-contamination between dialyzers and exposure of the operator opening the header cap, and reducing cost/time. Also, "single use" dialyzers with non-removable header caps can be cleaned.

Simple means (mechanical dislodgment) do not remove all contaminants required for reprocessing, thereby requiring hydrodynamic removal of at least some of the contaminants. The ID tip can also use fluid dynamics to suck clots into the ID sweep area to make them homogenized. This is especially important for dialyzers with O-rings and removable header caps. Previous techniques could cause O-ring chatter and force liquid behind the O-ring. The present invention can clean the O-ring area without direct physical contact. The area around the periphery (e.g., near the O-ring) can be especially hard to access and clean by conventional methods.

The ID is usually inserted through the existing (usually arterial) access port in the center of the header. This typically has a smooth cylindrical inner diameter of 3 mm, length of 6 to 10 cm, and is threaded on the outside. The access port is preferably as centered as possible.

Typical hollow fibers have a 0.2 mm internal diameter, an average pore size of 150 µm, and are made of polyethersulfone or polysulfone. The hollow fibers are typically puttied with polyurethane. This puttied surface with fiber ends is soft and easily abraded. Typical headers have dimensions of 2.0-2.5 cm. However, dialyzer header shapes can vary significantly, creating different flow streamlines, and often requiring different IDs and operating parameters.

In one embodiment, software is used to track dialyzers, their patients, and their number/quality of cleanings.

Liquid in the Header

The mechanical actions created by the rotation of the ID may be divided into two types, which may take place at the same time. The first type involves a direct transfer of some of the clots, contaminants and debris by direct attachment to the ID during rotation. The second type includes generation of hydrodynamic shear stresses due to rotation of the ID, and this is mostly created in the gap between the ID and surfaces of the cavity. The first action occurs in only some cases where the clots are large enough to touch the ID during rotation; thus, it is not an effective method to remove all clots from the dialyzer header. The second action, or the combination of the two, is preferred since the hydrodynamic shear stresses created by the ID rotation are uniform, and address the removal of all clots or contaminants present in the various locations of the header, including its ceiling surface. Therefore, it is necessary to ensure that sufficient liquid is present in the header in order to achieve optimal results.

Examination of dialyzer headers in a typical dialysis clinic reveals large variability with respect to the amount of liquid blood remaining in the headers after dialysis. The types of clots and their spatial distribution inside dialyzer headers are also very variable, as described in the examples. Our experience indicates that too little liquid in the header results in sub-optimal results with respect to the effectiveness of clot removal. Too much liquid in the header during ID rotation is preferred, but the excess liquid leads to overflow of liquid during ID rotation and to splattering of blood during the withdrawal of the ID from the header. The optimal liquid level was found when the ID was covered with liquid during rotation, and when the ID was fully engaged with the liquid to generate hydrodynamic shear stresses. The investigators determined that when the liquid was about 50% of header height, excellent cleaning results were achieved. This 50% level is arbitrary and may vary based on the dialyzer model and on the geometry of the cavity to be cleaned. In many cases, the dialyzer includes sufficient liquid to allow successful cleaning with the methods described in this invention. However, in some cases when the header was dry, some liquid had to be added (about 5 to 7 milliliters) to achieve good cleaning results.

Although adding RO water is sufficient to provide the fluid needed to achieve sufficient hydrodynamic stresses, other liquids may be preferred since they introduce additional functionalities regarding the removal of clots from dialyzer headers. Further, inclusion of certain additives in the liquid will enhance the cleaning processes. Additives appropriate for this application include surfactants, disinfecting agents, chelating agents, anti-clotting agents and pH-adjusting reagents. Surfactants such as the non-ionic series Tweens, for example Tween 20 and Tween 80, are known to be safe as parenteral additives. The non-ionic surfactants based on castor-oil ethoxylate, such as Cremophor EL, can also be added in the liquid used for header cleaning according to this invention. It may be desirable to include a rinsing step to remove surfactants. The following additives were found to be effective, including: citrates, gluconates, amino acids, heptoglucon-ates, sodiumtripolyphosphate, pyrophosphate, EDTA, NTA, sodium carbonate, saline solution, and heparin. The liquid compositions preferred for this application should also include a disinfectant acceptable for use in dialyzer reprocessing, including: peracetic acid, hypochlorite bleach and aldehydes. Alkaline pH of the solution to be used in the header is preferred since the high pH promotes dissolution of protein and other blood materials. Peracetic acid at high concentration should be avoided since it reacts violently with hemoglobin producing foam that hampers header cleaning according to this invention. Peracetic acid can create a foamy mixture out of the insertion port and, as a result, hamper cleaning. The preferred liquid composition according to this invention should include alkaline with pH above the isoelectric point of all known serum proteins (>11.3), and this can be achieved by the addition of NaOH or equivalent reagent, and should also include: a chelating agent such as citrates or EDTA, a disinfecting agent such as hypochlorite bleach, and optionally, a safe, non-foaming surfactant and anti-clotting agents such as heparin.

Other Applications

Many other applications of this invention are envisioned in addition to cleaning dialyzers. Some non-exclusive examples can include cleaning filters, membranes, nozzles, body cavities, etc. Surfaces can be textured, coatings can be applied, non-continuous coatings can be removed, surfaces can be cooled, etc. Some non-exclusive membrane examples can be for biopharma, cell separation, blood concentrate processing, virus filtration, oil/water separation, dispersion and filtration.

Many other surfaces beyond circles can be cleaned or modified. Some non-exclusive examples can include short tube interiors, heat exchangers, swimming pools, ear canals, spaces between parallel filter plates, etc. In cylindrical applications, the maximum fiber length will be limited by the stiffness of the ID, and therefore also the internal diameter of the cylinder.

EXAMPLES

The following examples will serve to further typify the nature of this invention, but should not be construed as a limitation in the scope thereof, which scope is defined solely by the appended claims.

Example 1

Gambro Polyflux hemodialyzers (dialyzers) (Models: 17R and 21R) were used to test methods, devices and other embodiments of the present invention. Some dialyzers were taken directly after the conclusion of dialysis treatment of actual patients, stored in the refrigerator for approximately 12 hours, and then left to sit out at room temperature for another 3 hours. Other dialyzers were taken immediately after the dialysis treatment of patients, stored in the refrigerator for approximately one hour, and then left to sit out at room temperature for another hour. All the dialyzers that were subjected to either method have adhering header clots where the clotting factors had enough time to form strong cross-linking resulting in the formation of fully formed blood clots. The clotted headers tested included clots with sufficient adhesion forces such that flushing them with water could not remove the clots by action of dissolution or simple detachment due to the presence of water. Each dialyzer was tested with the identical test procedure to assess the removal of header clots.

Types of Clots

Several hundred dialyzers were examined to identify the types of header clots and the difficulty in cleaning them during reprocessing. This classification helps identify limitations due to spatial distribution of clots and other factors such as adhesion of the clots to the surface of the header. We have been able to assign the various header clots into five categories as shown in FIG. 5:

Type A—This is characterized when the header is full of a single large blood clot. A clot of this type may include blood only, or in most cases comprised a fatty or white substance. Generally, this clot is dark and dense, and the details of the clotting structure and adhesion are generally not known, and vary with the history of the dialyzer and the blood chemistry of the patient. Also, the mechanical properties of this clot would depend on whether or not the patient is heparinized.

Type B—This type is identified when the blood clots do not occupy the entire header surface area and when the clots remain fixed to the puttied surface. This type does not include "ring" clots at the periphery of the header or clots that adhere to the underside of the header cap.

Type C—This is when there are clots formed at the periphery of the header. These clots tend to be the most difficult to remove due to stagnation regions arising from the shape of the header. These clots are generally very thin and have strong adhesion.

Type D—This is when a fatty or whitish substance forms small globules, and in some cases larger sized globules, on the puttied surface. The clots are generally opaque and yellowish-brown in color. The adhesion of these is generally lower than those consisting of dense blood. Many times clots of this type are mixed in with blood clots.

Type E—This is when there is dried or smeared blood on the underside (ceiling) surface of the header cap. There are two types generally seen in this class. The first looks like a smeared paste; the second appears like dried foam and are sponge-like in nature. These tend to be very difficult to remove and require the liquid level in the header to be at least 50% for effective cleaning Test Procedure: All the dialyzers described in the examples were used to perform full dialysis treatment, lasting approximately four hours, on actual patients. Also, all the dialyzers selected had stubborn header clots of various types, shapes, distribution and degrees of adhesion either to the puttied surface and/or the ceiling of the header cap. The examples provided represent the results of testing: cleaning conditions, ID geometry, ID materials, mode of operation and other manipulations needed to remove header clots of the various types.

In a typical header cleaning test, the dialyzer is first checked to ensure that all of its four caps (two for lumen ports and two for dialysate ports) are tightly closed and secured. The dialyzer is then placed in a vertical position, either held by hand or secured with the aid of a stand, and the cap of the upper blood port is carefully removed. To clean the clotted header, the ID is first secured to a mechanical rotating device to avoid slippage during rotation inside the header. The ID is then inserted into the dialyzer header so that its tip is in close proximity to the periphery of the dialyzer header, as detailed in the specification. The driving (motorized) device is turned on and the ID is allowed to rotate to create the fluid flows and mechanical stresses sufficient to detach the clots and break them down to a flowing liquid, an act called homogenization or dispersion. The header is subjected to this cleaning action for a period of time, normally lasting 5-15 seconds.

During the header cleaning tests, the ID was rotated with the aid of a commercial motorized device with RPM range of 5,000-35,000 (Dremel 300 Series). The minimum RPM tested was 5,000 (the lowest setting on the driving device); the maximum available in the above driving device was 35,000. Testing results indicate that ranges below and above this range can be used to achieve the desired results; therefore, the examples given are only guidelines for the selection of the proper RPM ranges, and are chosen for the case of header cleaning case. The selection of the mechanical conditions was dictated by requirements other than the mechanical forces elaborated in the invention. These other requirements include care to avoid damage to the dialyzer such as breakage or erosion of key components, as well as avoidance of exposing the worker to blood during the header cleaning operation. Thus, persons skilled in the art can use somewhat lower speed and longer time or higher speed and less time and other modes of performing the process to achieve the results as per the teachings of this invention. After approximately 5-15 seconds cleaning time, the driving device was turned off and the ID was carefully removed from the header to ensure minimum spilling, dripping, or splatter during this step. At the conclusion of the above steps, the port was re-capped and the dialyzer was inverted so that the other blood lumen port was now at the top, again in vertical orientation. The same cleaning process steps were repeated for this second header.

To assess the outcome of header-cleaning test, the dialyzer was rinsed with water and then examined visually as described above. In some tests, rinsing the header was also achieved by the back-flushing process where water was pressurized through one or both of the dialysate ports and exited via the header subjected to cleaning according to this invention. The header was deemed clean when all blood clots were detached from the interior surfaces of the header and could be flushed away from the dialyzer without the need to apply forces. No residues remain in the header at the location of the original clot were observed after cleaning according to the present invention. The dialyzer is then connected to reprocessing device to complete the cleaning of the fiber bundle, measure TCV and fiber leak, and then fill the dialyzer with an approved liquid sterilant like per-acetic acid, formaldehyde, or the like.

Example 2

In this example, the procedure of Example 1 was followed and several dialyzers were tested to assess the cleaning of header clots. The variable tested in this example was the effect of the rotational speed (expressed in RPM) on the degree of cleaning header clots. Cleaning of a header clot was deemed successful if the clot disappears (no trace could be seen visually) after subjecting the header to the cleaning operation with the rotating ID and then rinsing or displacing the homogenized blood with water as described above. The driving rotating device used was an off-the-shelf version (Dremel 300 Series) that had an RPM range of 5,000-35,000, divided into ten equal steps (3,000 RPM/step). Various speeds were tested and the preferred setting for cleaning dialyzer header was found to be in the lower end of the above range. Clot detachment, removal and homogenization were effectively accomplished in a short time of 5 to 15 second in the RPM range between 7,500 and 14,000. The ID used in this example was made from polypropylene and its dimensions were: 87 mm long, 4.14 mm wide at the shaft, 2.15 mm side at the insertion end, 1.05 mm thick at the shaft end, 0.5 mm thick at the insertion end. The ID tapered from 4.14 to 2.15 at the 66 mm mark.

These results showed that with an optimized ID (diameter and shape) (TBD) full header cleaning could be achieved at 5,000 to 7,500 RMP within 5 to 10 seconds. Our calculations, assuming optimal gap and ID geometry, placed the optimal RPM in the range of 1000-1500 RPM, or above. However, it appears that RPM >1000 may be needed to achieve full cleaning, especially in the cases of complex cavity shapes such as in the case of dialyzer headers. This above range represents the case of well adhering clots to the puttied surface of the dialyzer header. Based on the results it may be feasible to lower RPM or use longer time to clean less-adhering or less-formed clots as long as the fluid flow field in the header cavity can be achieved as described in the specification.

Example 3

In this example, the procedure from Example 1 was followed. The variable tested in this example was the cleaning time. In almost all cases (nine dialyzers and 18 headers), full header cleaning was accomplished in 5 seconds. In one or two cases, as much as 15 seconds was needed to achieve full clot removal, specifically clots of Type E (FIG. 5), where part of the clot is located on the ceiling of the header surface. With the optimized ID and proper RPM as defined in Example 2, all headers were fully cleaned in the 5-10 second range. The smear is more difficult than the spongy type. The cleaning was difficult due to the fact that the clot was on the ceiling. Puttied surface clots are generally very easy to remove. The liquid level was sufficient in these cases, although, a few more milliliters of liquid might have made a difference.

Example 4

In this example, the procedure from Example 1 was followed. The variables tested in this example were related to the geometry and materials of the ID. In one test, a piece of hollow Teflon tubing (length=88 mm; width/thickness=1.5 mm) was used as the ID. The test immediately proved that this type of tubing lacked the rigidity necessary for the ID in this application. The tube deformed during insertion into the dialyzer header, even before the driving device turned on. The tubing was prone to multiple kinking, and could be bent or shaped to provide the ID necessary for header cleaning as described in the specification. Turning on the rotary device at 7500 RPM resulted in destroying the tubing inside the header. It was determined that this type of hollow tubing that lacks sufficient rigidity is not acceptable for use as an ID.

The second ID tested was a piece of solid polyethylene (87 mm long, 4.14 mm wide at the shaft, 2.15 mm side at the insertion end, 1.05 mm thick at the shaft end, 0.5 mm thick at the insertion end. The ID tapered from 4.14 to 2.15 at the 66 mm mark). This proved to be effective, even when less optimal shape and size was used. The square shape of this material (polyethylene) was found to lead an ID failure when used at high RPM (in excess of 10,000 RPMs). The square or rectangular cross section ID shaft was not able to turn inside the dialyzer lumen orifice, where the ID enters the header. This ID got snagged in this orifice and was then torn apart when rotated at high speed (in excess of 10,000 RPMs). The solution to this problem was to design the shaft of the ID to be cylindrical, at least at the position where it would freely rotate in the lumen orifice, without friction (FIG. 1a).

Example 5

In this example, the procedure from Example 1 was followed. The variable tested in this example was related to the preferred mechanical action of ID during the cleaning of header clots. During testing, it was determined that if the ID was moved slowly up and down while it was rotating during cleaning, clot removal was more easily accomplished compared to if it was kept in a single position. The effect of this up and down motion appears to result in more agitation or stronger hydrodynamic action inside the header due to the lateral and vertical action of the ID. This alternating action also ensures that the ID reaches the periphery of the header and removes all clots of Type C (FIG. 5). This mode of manipulation also ensures that there is full wetting of the header region so that a mechanical action is produced at all available header surface, including and especially the underside (ceiling) of the header cap, for removal of clots of Type E (FIG. 5).

Example 6

Figure 6:
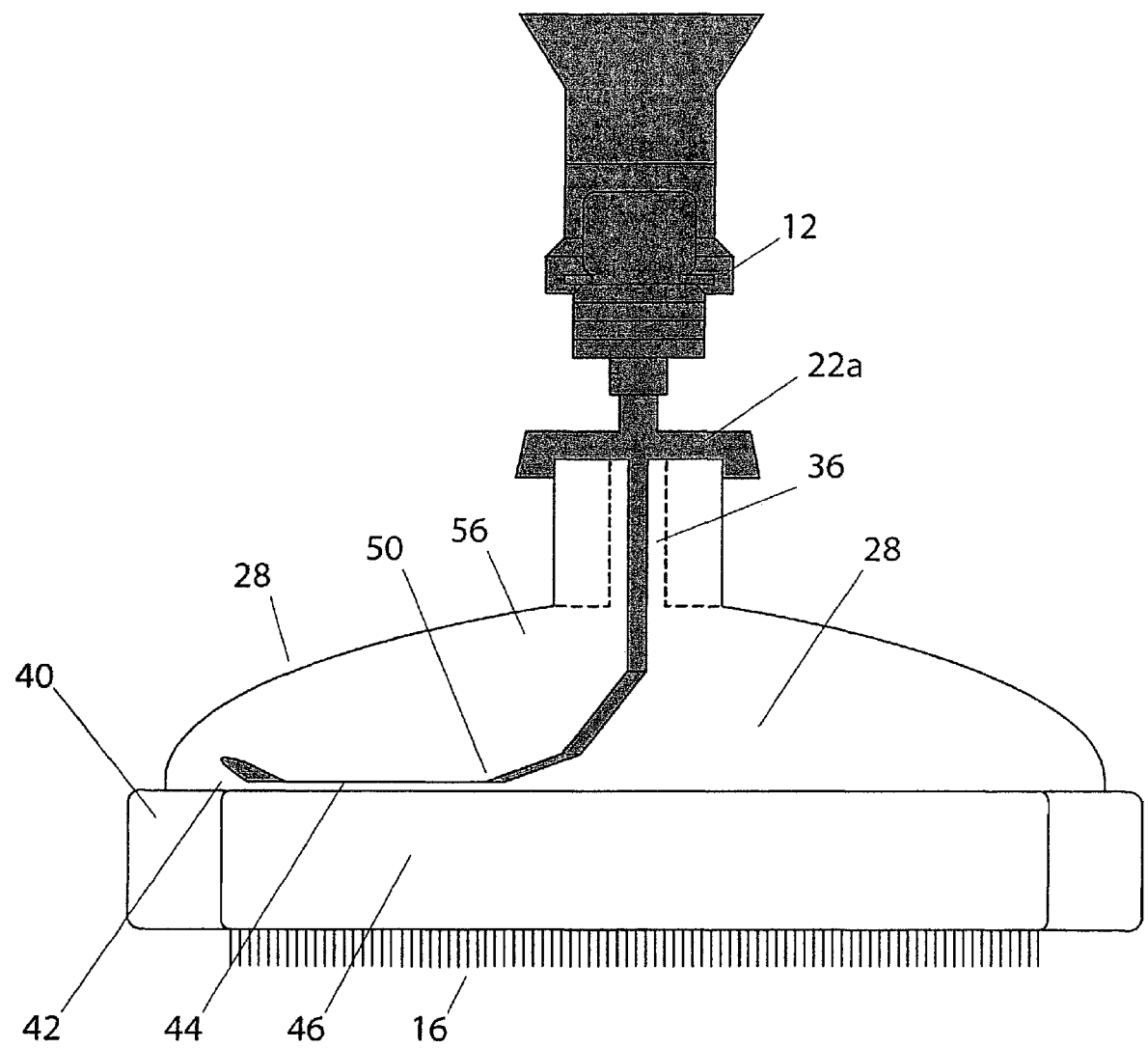
FIG. 6 is a schematic of an insertion device that caps the top of the dialyzer port.
Figure 7:
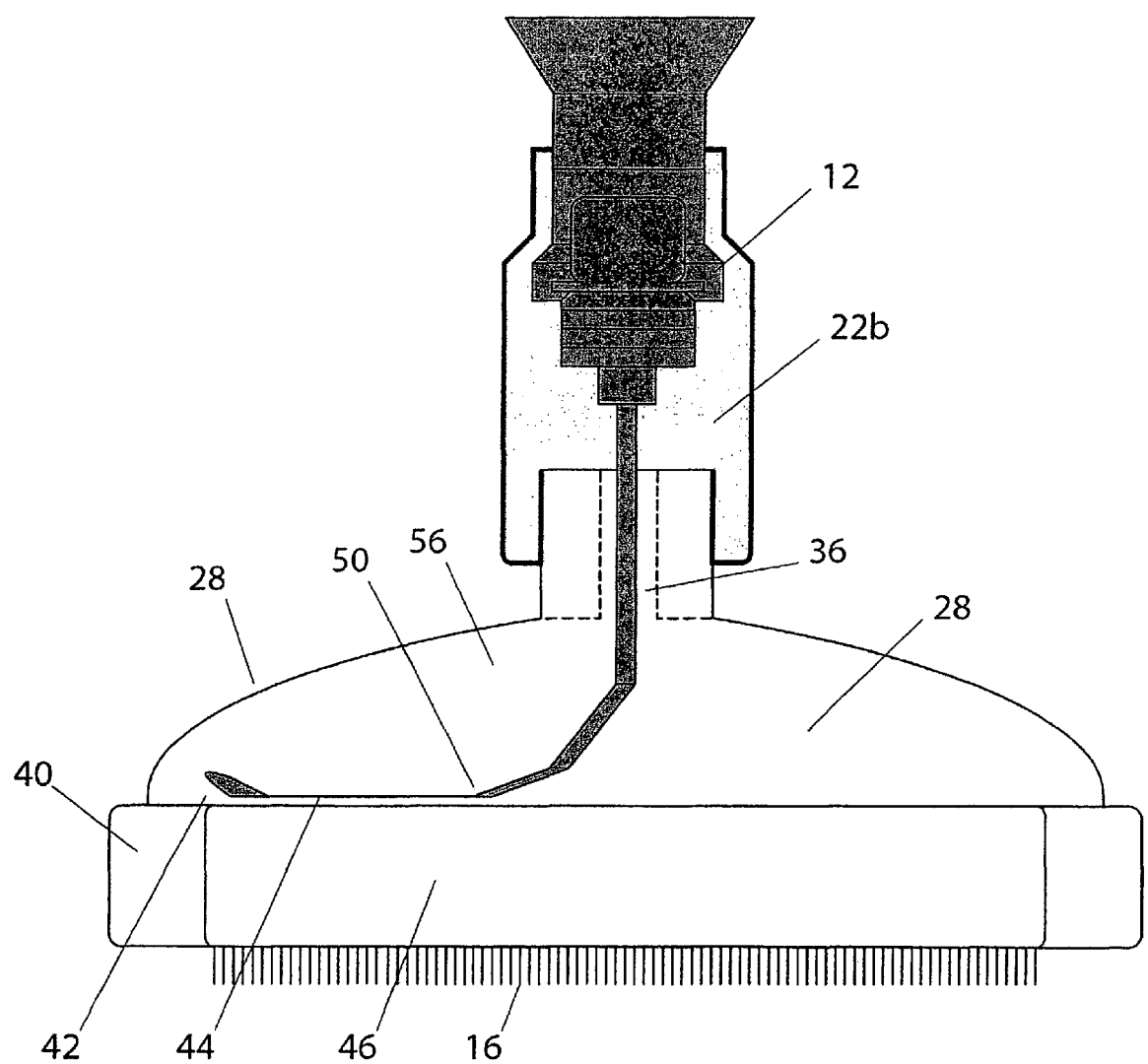
FIG. 7 is a schematic of a rubber boot that slips over the dialyzer port to prevent splashing.

In this example, the procedure from Example 1 was followed. The tests performed in this example related to the need of a splashguard as a part of the invention. In one test, the homogenized blood mixture in the header sprayed out of the header due to ID rotation. The results of our testing have clearly indicated that a splashguard needs to be incorporated into the driving device or be a part of the ID itself. There are at least four ways for preventing the splashing blood during the entire header cleaning according to the embodiments of this invention. First, the ID itself can include a cap 22a over the top of the dialyzer port (FIG. 6). This method might not work if the device were to incorporate a pulsating action. The second case would be to place a rubber boot 22b that slips over the dialyzer port (FIG. 7). The third method would be to use an external splashguard 22 in some kind of umbrella configuration (FIG. 2). The fourth method would be to design the ID and device such that the device screwed into the existing threaded dialyzer port. This method would seal the header region and eliminate any chance for splashing.

Example 7

In this example, the procedure from Example 1 was followed. This example provides information regarding the need for a minimum volume of liquid inside the header to achieve optimal cleaning. This is important since a portion of the dialyzer to be reprocessed does not have enough blood or liquid in the header to ensure best header cleaning conditions according to the present invention. In certain cases, dialyzers tested had headers that contained clots or other bulk patient material but no liquid. The ID rotation was not optimal in removing such clots without a liquid to at least partially full header. The results of this testing indicated that the header must be filled to at least 50% with a liquid. RO water or other liquid can be used to achieve this result. The amount of liquid required to fill a dialyzer header is 5-7 ml for a 17R dialyzer and 7-9 ml for a 21R dialyzer.

Example 8

In this example, the procedure from Example 1 was followed. In some cases, clots or other patient materials become attached to the underside (ceiling) of the dialyzer header cap. These clots (FIG. 5—Type E) are very difficult to remove without the use of the proper ID geometry, RPM, time, liquid volume in the header and pulsating action. It is important to note that this type of clots can only be removed by the hydrodynamic action and forces on the liquid flow field created by the ID rotation inside the header, as previously described. For this reason, it is important that the dialyzer header be filled with a liquid to at least 50% of its volume. This enables the hydrodynamic action and forces to reach these difficult to access clots. The same requirements apply to other areas where the ID could not reach, especially for peripheral clots such as Type C and Type E (FIG. 5).

Example 9

In this example, the procedure from Example 1 was followed. This example is related to liquid retention on the ID surface and means to minimize splatter while removing it from the header after the conclusion of the cleaning procedure. Liquid/blood retention on the surface of the ID was closely monitored during our testing. When the ID is removed from the header, it should retain as little blood or patient material as possible to prevent splashing. We tested several ID materials to define the needed requirements with respect to blood retention on the ID surface and found that that ID material should be chosen with a very high hydrophobicity. Teflon and polyethylene were better than acrylics and polyurethane. This may be related to the wetting and the contact ability of the ID materials to be used. It also appears that cylindrical smooth ID is better than rectangular rough surface, even with the same dimensions.

The above specification, example and data provide a complete description of the manufacture and use of the composition of the invention. Since many embodiments of the invention can be made without departing from the spirit and scope of the invention, the invention resides in the claims hereinafter appended.

We claim:

1. A method for cleaning interior surfaces of a header region of a hemodialyzer defined by a header surface and a header region wall, the method comprising:
(a) introducing an insertion device having an end portion and a shaft through a hemodialyzer blood port so that the end portion of the insertion device is within the header region, wherein the shaft has a bend so that the end portion extends toward the header region wall forming a tip gap between the end portion and the header region wall, and forming a main gap between the shaft and the header surface;

(b) rotating the shaft at a speed sufficient to generate mechanical stresses for the removal of contaminants from interior surfaces of the header region;

(c) removing the insertion device from the header region; and (d) rinsing and flushing away the removed contaminants from the header region.

2. A method according to claim 1 wherein the header region includes liquid sufficient to cover the end portion of the insertion device during rotation.

3. A method according to claim 1 wherein the end portion comprises a non-abradable polymer.

4. A method according to claim 1 wherein the end portion is a hydrophobic polymer.

5. A method according to claim 1 wherein the end portion is smooth.

6. A method according to claim 1 wherein the rotational speed is more than 100 rpm.

7. A method according to claim 1 wherein the rotational speed is between 5,000 and 15,000 rpm.

8. A method according to claim 1 wherein the contaminants comprise blood clots.

9. A method according to claim 1 wherein the contaminants comprise patient materials.

10. A method according to claim 1 wherein at least a portion of the contaminants is removed by attachment to the rotating end portion.

11. A method according to claim 1 wherein the insertion device forms a narrow gap relative to the header surface during rotation.

12. A method according to claim 11 wherein the shear stresses generated in the gap between the header surface and the end portion of the insertion device is higher than outside the gap.

13. A method according to claim 1 wherein the rotation speed generates a shear stress of at least 3 Pa.

14. A method according to claim 1 wherein the rotation speed generates a shear stress of more than 10 Pa.

15. A method according to claim 1 wherein the rotation speed generates a shear stress more than 14 Pa.

16. A method according to claim 1 wherein the header region includes a sufficient volume of liquid to generate hydrodynamic shear stresses.

17. A method according to claim 1 wherein the end portion is shaped to form a narrow gap with most of the header surface.

18. A method according to claim 1 wherein the end portion length is sufficient to generate shear stress at the periphery of the header region during rotation.

19. A method according to claim 1 wherein the stiffness of the end portion is high enough to prevent deflection during rotation.

20. A method according to claim 1 wherein the axial force applied to the end portion is enough to form a narrow main gap with the header surface.

21. A method according to claim 1 wherein the axial force applied to the end portion is adjusted to prevent contact of the flexible member with the header surface.

22. A method according to claim 1 wherein the cleaning time is at least 5 seconds.

* * * * *